(12) United States Patent
Kaczorowski

(10) Patent No.: US 10,441,774 B2
(45) Date of Patent: Oct. 15, 2019

(54) DEVICES FOR ENDOVASCULAR ACCESS THROUGH EXTRACORPOREAL LIFE SUPPORT CIRCUITS

(71) Applicant: ECMOtek, LLC, York, PA (US)

(72) Inventor: David Kaczorowski, York, PA (US)

(73) Assignee: ECMOTEK, LLC, York, PA (US)

( * ) Notice: Subject to any disclaimer, the term of this patent is extended or adjusted under 35 U.S.C. 154(b) by 97 days.

(21) Appl. No.: 15/338,019

(22) Filed: Oct. 28, 2016

(65) Prior Publication Data

US 2017/0120033 A1 May 4, 2017

Related U.S. Application Data

(60) Provisional application No. 62/248,525, filed on Oct. 30, 2015.

(51) Int. Cl.
*A61M 39/10* (2006.01)
*A61B 17/34* (2006.01)
(Continued)

(52) U.S. Cl.
CPC ..... *A61M 39/1055* (2013.01); *A61B 17/3423* (2013.01); *A61M 1/1698* (2013.01);
(Continued)

(58) Field of Classification Search
CPC ............ A61M 39/1055; A61M 1/3659; A61M 1/1698; A61M 1/3653; A61B 17/3423
(Continued)

(56) References Cited

U.S. PATENT DOCUMENTS 3,565,074 A 2/1971 Philip
4,000,739 A 1/1977 Stevens
(Continued)

FOREIGN PATENT DOCUMENTS

EP 0411605 A1 2/1991
WO WO2015089047 A1 6/2015

OTHER PUBLICATIONS

Squiers JJ, Lima B, DiMaio JM. Contemporary extracorporeal membrane oxygenation therapy in adults: Fundamental principles and systematic review of the evidence. J Thorac Cardiovasc Surg. Jul. 2016;152(1):20-32.
(Continued)

*Primary Examiner* — Phillip A Gray
(74) *Attorney, Agent, or Firm* — Carothers and Carothers

(57) ABSTRACT

Adaptors, cannulas, caps, tube couplers, and systems thereof provide endovascular access through an established ECLS system. Adaptors having curved or angled shafts navigate right angle side ports of standard bypass cannulas and permit hemostatic introduction and direction of an intervention device to the axial flow path of the cannula lumen and bypass system. A modified cannula having an angled side port is also provided for use as an arterial cannula. A cap having an occluding surface may be inserted into the angled side port to prevent blood from stagnating in the angled side port. A tube coupler is also provided having an access port, such as an angled access port, and may be spliced into an established bypass system for vascular access point. Multiple couplers can be used to provide multiple access points. The adaptors and occlusive cap are interchangeable with each other and with secondary circuits.

7 Claims, 13 Drawing Sheets

(51) Int. Cl.
*A61M 39/20* (2006.01)
*A61M 1/16* (2006.01)
*A61M 1/36* (2006.01)

(52) U.S. Cl.
CPC ........ *A61M 1/3653* (2013.01); *A61M 1/3655* (2013.01); *A61M 1/3659* (2014.02); *A61M 39/10* (2013.01); *A61M 39/105* (2013.01); *A61M 39/20* (2013.01); *A61M 1/3666* (2013.01); *A61M 2039/1077* (2013.01)

(58) Field of Classification Search
USPC .......................................................... 604/256
See application file for complete search history.

(56) References Cited

U.S. PATENT DOCUMENTS

| | | |
|---|---|---|
| 4,054,136 A | 10/1977 | Zeppelin |
| 4,099,528 A | 7/1978 | Sorenson et al. |
| 4,143,853 A | 3/1979 | Abramson |
| 4,149,535 A | 4/1979 | Volder |
| 4,177,814 A | 12/1979 | Knepshield et al. |
| 4,235,232 A | 11/1980 | Spaven et al. |
| 4,287,892 A | 9/1981 | Schiff |
| 4,318,401 A | 3/1982 | Zimmerman |
| 4,334,551 A | 6/1982 | Pfister |
| 4,424,833 A | 1/1984 | Spector et al. |
| 4,430,081 A | 2/1984 | Timmermans |
| 4,468,224 A | 8/1984 | Enzmann et al. |
| 4,578,057 A | 3/1986 | Sussman |
| 4,580,573 A | 4/1986 | Quinn |
| 4,610,665 A | 9/1986 | Matsumoto et al. |
| 4,634,432 A | 1/1987 | Kocak |
| 4,655,752 A | 4/1987 | Honkanen et al. |
| 4,730,616 A | 3/1988 | Frisbie et al. |
| 4,804,365 A | 2/1989 | Litzie et al. |
| 4,826,477 A | 5/1989 | Adams |
| 4,886,507 A | 12/1989 | Patton et al. |
| 4,944,729 A | 7/1990 | Buckberg et al. |
| 4,960,412 A | 10/1990 | Fink |
| 4,994,027 A | 2/1991 | Farrell |
| 5,009,636 A | 4/1991 | Wortley et al. |
| 5,011,469 A | 4/1991 | Buckberg et al. |
| 5,066,285 A | 11/1991 | Hillstead |
| 5,125,902 A | 6/1992 | Berry et al. |
| 5,171,218 A | 12/1992 | Fonger et al. |
| 5,186,713 A | 2/1993 | Raible |
| 5,209,741 A | 5/1993 | Spaeth |
| 5,254,097 A | 10/1993 | Schock et al. |
| 5,256,150 A | 10/1993 | Quiachon et al. |
| 5,290,249 A | 3/1994 | Foster et al. |
| 5,300,023 A | 4/1994 | Lowery et al. |
| 5,312,344 A | 5/1994 | Grinfield |
| 5,330,433 A | 7/1994 | Fonger |
| 5,330,451 A | 7/1994 | Gabbay |
| 5,352,215 A | 10/1994 | Thome et al. |
| 5,395,341 A | 3/1995 | Slater |
| 5,395,352 A | 3/1995 | Penny |
| 5,417,665 A | 5/1995 | De La Mata et al. |
| 5,451,207 A | 9/1995 | Yock |
| 5,478,309 A | 12/1995 | Sweezer et al. |
| 5,520,655 A | 5/1996 | Davila et al. |
| 5,584,803 A | 12/1996 | Stevens et al. |
| 5,613,956 A | 3/1997 | Patterson |
| 5,669,881 A | 9/1997 | Dunshee |
| 5,702,368 A | 12/1997 | Stevens |
| 5,702,370 A | 12/1997 | Sylvanowicz et al. |
| 5,769,816 A | 6/1998 | Barbut |
| 5,779,681 A | 7/1998 | Bonn |
| 5,785,693 A | 7/1998 | Haining |
| 5,788,676 A | 8/1998 | Yoon |
| 5,797,888 A | 8/1998 | Yoon |
| 5,863,366 A | 1/1999 | Snow |
| 5,868,703 A | 2/1999 | Bertolero |
| 5,935,110 A | 8/1999 | Brimhall |
| 5,944,019 A | 8/1999 | Knudson |
| 6,029,671 A | 2/2000 | Stevens et al. |
| 6,083,215 A | 7/2000 | Milavetz |
| 6,095,997 A | 8/2000 | French et al. |
| 6,099,506 A | 8/2000 | Macoviak et al. |
| 6,120,480 A | 9/2000 | Zhang et al. |
| 6,142,446 A | 11/2000 | Leinsing |
| 6,228,071 B1 | 5/2001 | Moshe et al. |
| 6,238,404 B1 | 5/2001 | Hidalgo et al. |
| 6,240,960 B1* | 6/2001 | Fillmore ............... A61F 5/4405 137/607 |
| 6,458,103 B1 | 10/2002 | Albert et al. |
| 6,482,171 B1 | 11/2002 | Corvi et al. |
| 6,514,236 B1 | 2/2003 | Stratienko |
| 6,569,117 B1 | 5/2003 | Ziv et al. |
| 6,620,124 B1 | 9/2003 | Peavey |
| 6,673,040 B1 | 1/2004 | Samson et al. |
| 6,716,189 B1 | 4/2004 | Jarvik |
| 6,802,836 B2 | 10/2004 | Bouphavichith et al. |
| 6,808,508 B1 | 10/2004 | Zafirelis et al. |
| 6,821,287 B1 | 11/2004 | Jang |
| 6,905,481 B2 | 6/2005 | Sirimanne |
| 6,913,021 B2 | 7/2005 | Knudson et al. |
| 7,093,859 B2 | 8/2006 | Warburton-Pitt et al. |
| 7,473,239 B2 | 1/2009 | Wang et al. |
| 7,651,481 B2 | 1/2010 | Raybuck |
| 7,766,853 B2 | 8/2010 | Lane |
| 7,854,731 B2 | 12/2010 | Rome et al. |
| 7,914,519 B2 | 3/2011 | Moran et al. |
| 8,177,770 B2 | 5/2012 | Rasmussen et al. |
| 8,177,771 B2 | 5/2012 | Butts et al. |
| 8,267,897 B2 | 9/2012 | Wells |
| 8,286,657 B2 | 10/2012 | Belley et al. |
| 8,308,692 B2 | 11/2012 | McQueen |
| 8,308,713 B2 | 11/2012 | Li et al. |
| 8,357,122 B2 | 1/2013 | Kraus et al. |
| 8,372,072 B2 | 2/2013 | Lindenbaum et al. |
| 8,398,612 B2 | 3/2013 | Frey et al. |
| 8,412,300 B2 | 4/2013 | Sonderegger |
| 8,444,602 B2 | 5/2013 | Valaie |
| 8,562,519 B2 | 10/2013 | Smith et al. |
| 8,585,660 B2 | 11/2013 | Murphy |
| 8,617,138 B2 | 12/2013 | Barron et al. |
| 8,720,065 B2 | 5/2014 | Christensen et al. |
| 8,747,387 B2 | 6/2014 | Belley et al. |
| 8,753,317 B2 | 6/2014 | Osborne et al. |
| 9,205,244 B2 | 12/2015 | Valaie |
| 9,278,188 B2 | 3/2016 | King |
| 2002/0087127 A1 | 7/2002 | Finch et al. |
| 2003/0032969 A1 | 2/2003 | Gannoe et al. |
| 2005/0171479 A1 | 8/2005 | Hruska et al. |
| 2005/0209584 A1 | 9/2005 | Rome |
| 2005/0245868 A1 | 11/2005 | Olsen et al. |
| 2006/0089604 A1 | 4/2006 | Guerrero |
| 2008/0147012 A1 | 6/2008 | Rome |
| 2008/0179882 A1 | 7/2008 | Hanlon et al. |
| 2009/0005725 A1 | 1/2009 | Shorey |
| 2009/0241963 A1 | 10/2009 | Macmillan |
| 2010/0241068 A1 | 9/2010 | Chen |
| 2011/0040241 A1 | 2/2011 | Wang et al. |
| 2011/0071502 A1* | 3/2011 | Asai .................. A61M 25/0606 604/528 |
| 2012/0123392 A1 | 5/2012 | McKinnon et al. |
| 2013/0237925 A1* | 9/2013 | Trainer ............ A61M 25/0097 604/247 |
| 2013/0310767 A1 | 11/2013 | Solar et al. |
| 2014/0221968 A1 | 8/2014 | Ransbury et al. |
| 2014/0236088 A1 | 8/2014 | Rashdan et al. |
| 2014/0275724 A1 | 9/2014 | Wang et al. |
| 2015/0133720 A1 | 5/2015 | Farnan et al. |
| 2016/0015955 A1 | 1/2016 | Joseph et al. |

OTHER PUBLICATIONS

Hill JD, O'Brien TG, Murray JJ, Dontigny L, Bramson ML, Osborn JJ, Gerbode F. Prolonged extracorporeal oxygenation for acute post-traumatic respiratory failure (shock-lung syndrome). Use of

(56) References Cited

OTHER PUBLICATIONS the Bramson membrane lung. N Engl J Med. Mar. 23, 1972;286(12):629-34.

Australia and New Zealand Extracorporeal Membrane Oxygenation (ANZ ECMO) Influenza Investigators, Davies A, Jones D, Bailey M, Beca J, Bellomo R, Blackwell N, Forrest P, Gattas D, Granger E, Herkes R, Jackson A, McGuinness S, Nair P, Pellegrino V, Pettilä V, Plunkett B, Pye R, Torzillo P, Webb S, Wilson M, Ziegenfuss M. Extracorporeal Membrane Oxygenation for 2009 Influenza A(H1N1) Acute Respiratory Distress Syndrome. JAMA. Nov. 4, 2009;302(17):1888-95.

Lawler PR, Silver DA, Scirica BM, Couper GS, Weinhouse MD, Camp PC Jr. Extracorporeal Membrane Oxygeneation in Adults With Cardiogenic Shock. Circulation. 2015; 131:676-680.

International Searching Authority; International Search Report and Written Opinion of the International Searching Authority; International Application No. PCT/US2016/059546; Patent Cooperation Treaty; pp. 1-8; publisher United States International Searching Authority; Published Alexandria, Virginia, US; copyright and dated Jan. 3, 2017; (8 pages).

International Searching Authority; International Search Report and Written Opinion of the International Searching Authority; International Application No. PCT/US2016/059562; Patent Cooperation Treaty; pp. 1-9; publisher United States International Searching Authority; Published Alexandria, Virginia, US; copyright and dated Jan. 3, 2017; (9 pages).

International Searching Authority; International Search Report and Written Opinion of the International Searching Authority; International Application No. PCT/US2016/059570; Patent Cooperation Treaty; pp. 1-9; publisher United States International Searching Authority; Published Alexandria, Virginia, US; copyright and dated Jan. 3, 2017; (9 pages).

* cited by examiner

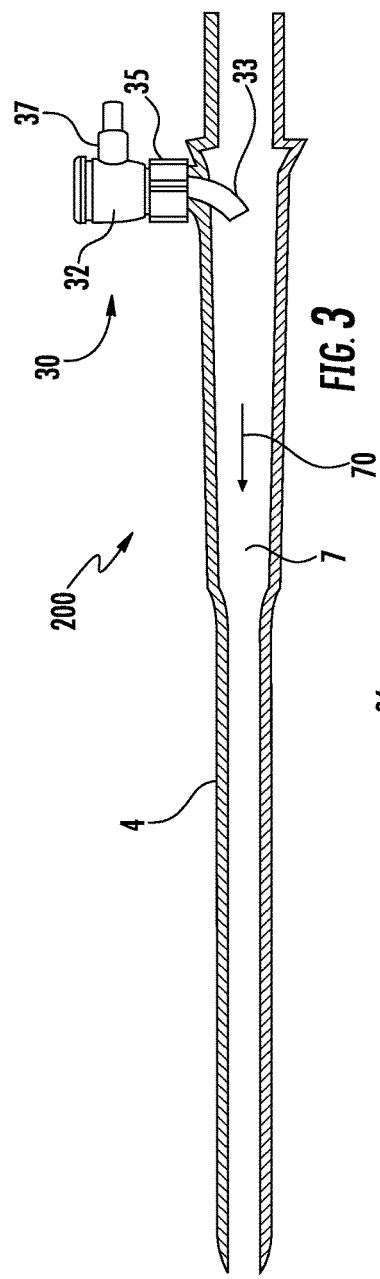
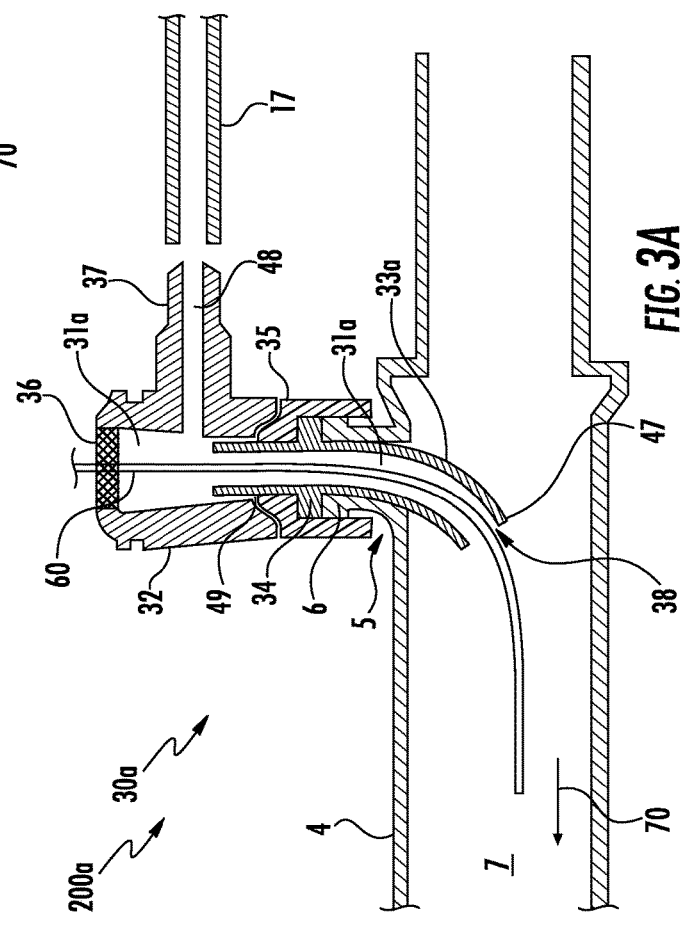
FIG. 3
FIG. 3A

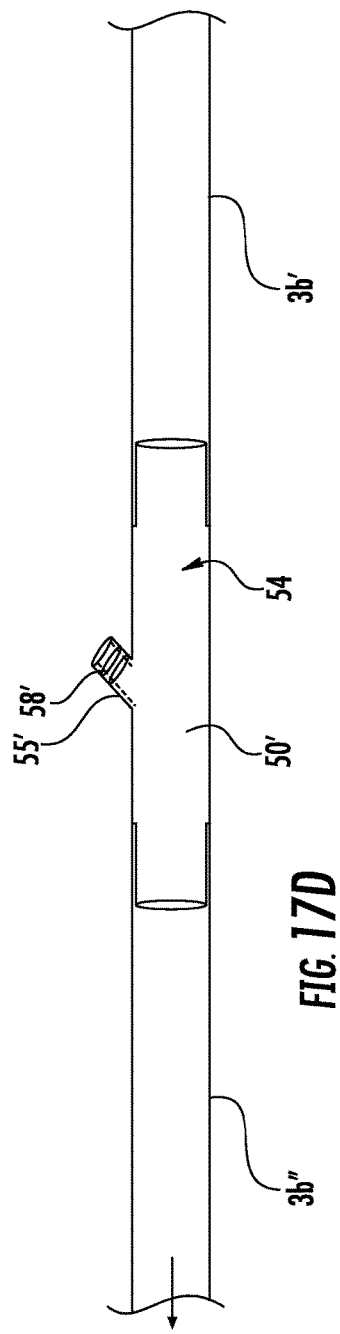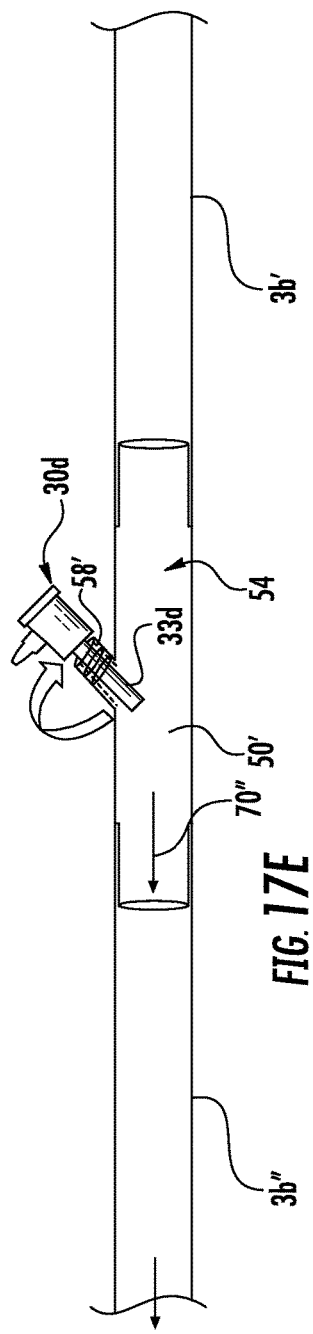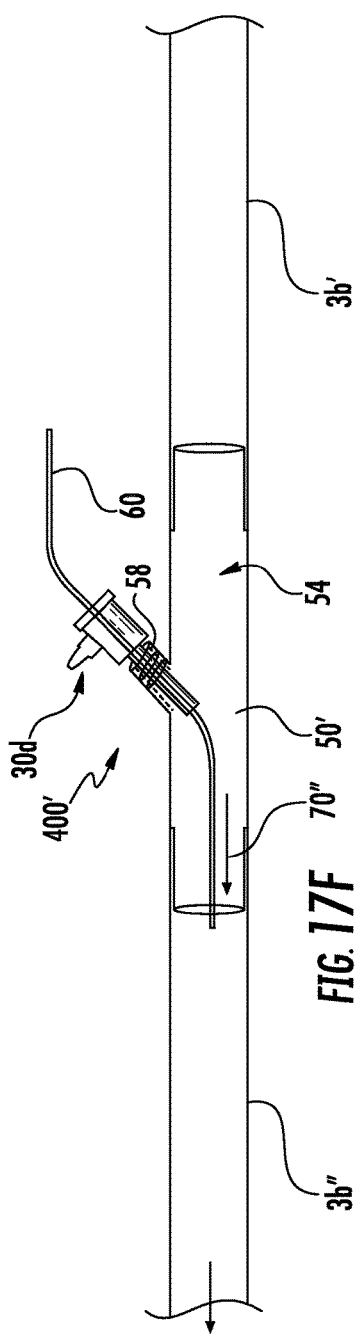

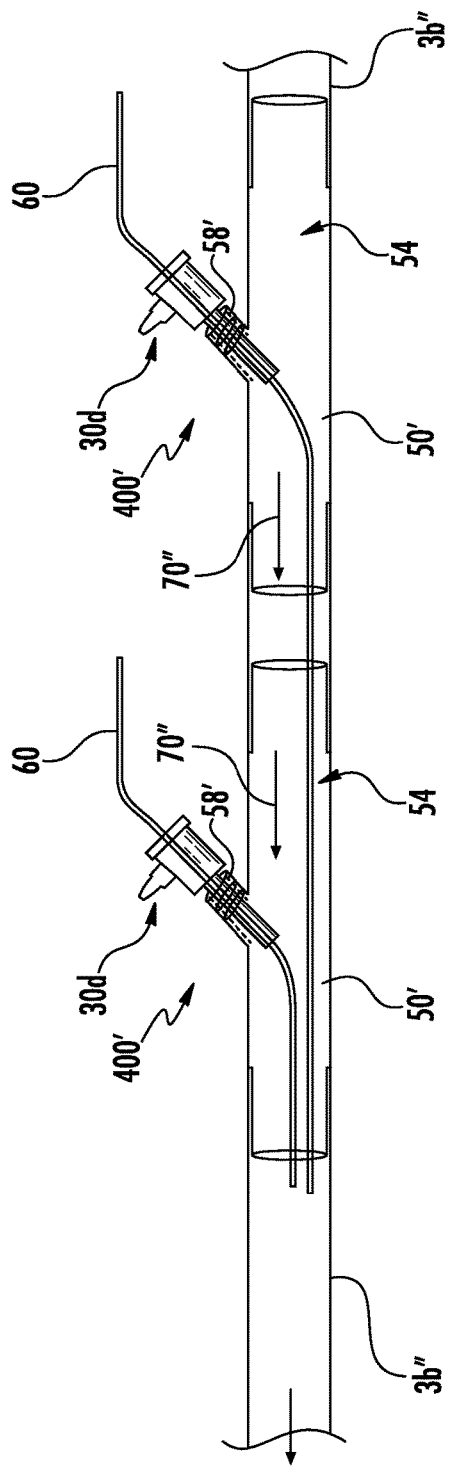
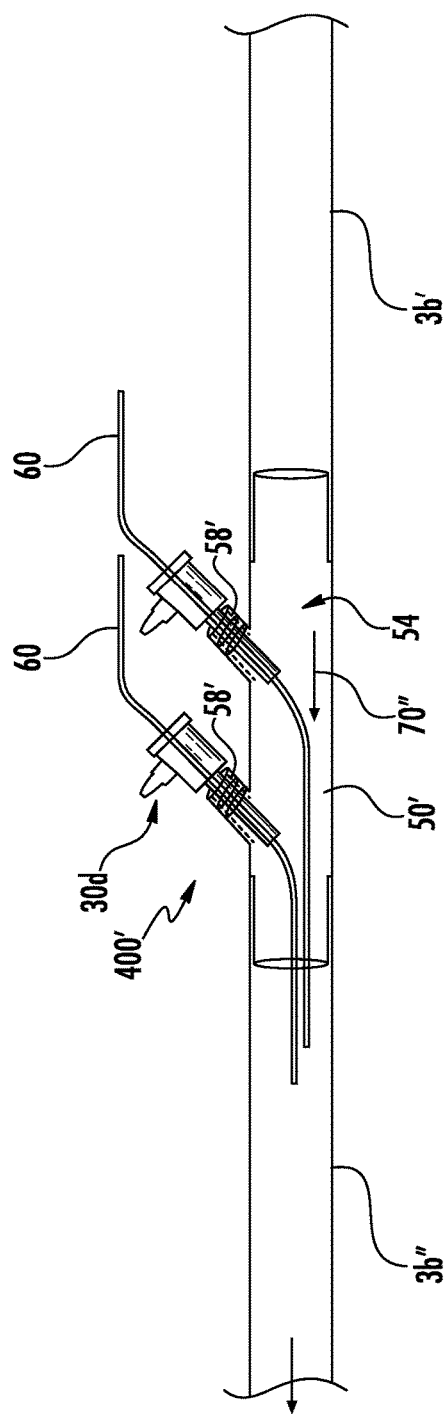
FIG. 18
FIG. 19

DEVICES FOR ENDOVASCULAR ACCESS THROUGH EXTRACORPOREAL LIFE SUPPORT CIRCUITS

CROSS-REFERENCE TO RELATED APPLICATIONS

The present application claims the benefit of U.S. Provisional Application having Ser. No. 62/248,525, filed on Oct. 30, 2015, the contents of which are incorporated by reference herein in its entirety.

FIELD OF THE INVENTION

This invention relates to devices for accessing the interior of a subject, such as the vascular system, through extracorporeal life support (ECLS) system components, such as extracorporeal membrane oxygenation ("ECMO") circuits. More in particular, it relates to cannulas, adaptors, sheaths, tubing, connectors and other medical devices for use as or in connection with bypass system components to gain entry to the vascular system through the bypass system, such as an ECMO circuit.

BACKGROUND

Extracorporeal membrane oxygenation ("ECMO") is a form of cardio-pulmonary bypass that is employed to support critically ill patients with acute cardiac failure, respiratory failure, or combined cardiopulmonary failure. A typical ECMO circuit 100 as shown in FIG. 1 consists of multiple components including cannulas, tubing, an oxygenator, and pump with a controller. A heater-cooler element may be added for temperature management as well. Generally, a venous cannula 2 is inserted either into a large vein, such as a femoral vein, or the right atrium of the heart for drainage of blood from the patient. The blood is carried via bypass tubing 3a to a pump (not shown), which provides forward flow through the circuit, and to an oxygenator (not shown), which both oxygenates the blood and allows removal of carbon dioxide. The blood is then returned to the patient via bypass tubing 3b connected to a return or arterial cannula 4, which is generally placed in either the aorta or a large peripheral vessel, such as the femoral artery. Depending on the configuration, an ECMO circuit can provide gas exchange for patients with acute pulmonary failure, or both gas exchange and hemodynamic support for patients with acute cardiac or combined cardiopulmonary failure. In the setting of acute cardiac and pulmonary failure, ECMO can provide immediate restoration of perfusion and oxygen delivery to tissues, thereby preventing worsening acidosis, shock, multisystem organ failure and ultimately death and allowing for time for either organ recovery or diagnosis and intervention.

Use of this form of temporary mechanical circulatory support was initially reported in 1972. Since its introduction, technological advances in all components of the ECMO circuit have occurred. For example, improved cannula design has allowed more facile insertion with less trauma to blood vessels. Advances in pump and oxygenator design have allowed for greater efficiency and less trauma to blood elements. In the context of these advances, it was discovered that ECMO could serve as a valuable tool in supporting critically ill patients afflicted with H1N1 influenza. In its most severe manifestations, H1N1 was associated with a high mortality rate and it was found that ECMO could reduce mortality in these critically ill patients. Improvements in ECMO technology, along with its demonstrated success with critically ill H1N1 patients, have led to a dramatic growth in the use of ECMO for patients with acute cardiopulmonary failure.

ECMO is generally considered to be a supportive technology intended to provide oxygen and hemodynamic support to patients with acute cardio-pulmonary failure through a closed system. Many patients that require ECMO also require invasive procedures for diagnosis and potentially intervention. Many of these procedures, such as left and right heart catheterization, percutaneous coronary intervention, or insertion of catheters for instillation of thrombolytics, require access to the cardiovascular system, which is usually established by inserting an introducer sheath into a peripheral vessel after obtaining access with a needle. However, institution of ECMO generally requires thorough systemic anticoagulation to increase blood flow and prevent clotting. Anticoagulation, however, complicates obtaining access to the vascular system for other subsequent diagnostic and therapeutic procedures, as the anticoagulants cause an increased risk of bleeding when attempting to access a vessel. Furthermore, vascular access is often obtained in the clinical setting by palpating a patient's pulse as a landmark for locating the blood vessel. ECMO provides laminar flow and a patient on ECMO may have very little or no difference in systolic or diastolic blood pressure, resulting in a very low pulse pressure. While a patient may have adequate blood pressure, there may be very little pulsatility and it may be difficult or impossible to palpate a pulse while on ECMO. Thus, despite the potential necessity for vascular access for subsequent diagnostic and therapeutic procedures while on ECMO, obtaining vascular access in patients on ECMO may be challenging and result in complications including vascular injury and bleeding.

Since establishment of an ECMO circuit requires insertion of cannulas into the vascular system, the ECMO circuit itself has the potential to serve as an access point to the cardiovascular system and allow the performance of diagnostic and therapeutic procedures to promote the recovery of the patient. Utilizing the ECMO circuit itself for access to the cardiovascular system would circumvent the challenges and risks associated with attempting to access another blood vessel. However, an ECMO circuit is generally not used as a vascular access point in clinical practice as a safe and facile means of doing so does not exist with currently available technology.

For example, the arterial or in-flow cannula 4 generally represents the most proximate component of the ECMO circuit to the patient's cardiovascular system. This arterial cannula 4 is typically inserted into a large peripheral vessel, such as the femoral or axillary artery, or directly into the aorta. Most commercially produced cannulas have a small, perpendicular side port 5 with a Luer connector, as shown in FIG. 1. This side port 5 allows air to be eliminated from the circuit and also allows for establishment of a secondary circuit, such as for perfusion of blood to the ipsilateral limb. Such secondary circuits are established by a secondary circuit connector 13 attaching to the side port 5 of the arterial cannula. Secondary circuit tubing 14 directs blood from the side port 5 to a superficial cannula 10, such as a superficial femoral arterial cannula. Both the main arterial cannula 4 and the superficial cannula 10 may be introduced into the artery at the same insertion point 12, with the cannula 4 being directed toward the heart, and the superficial cannula 10 being directed toward the ipsilateral limb, such as the leg in a femoral arterial setting. The secondary circuit therefore allows perfusion into the ipsilateral leg and prevents ischemia and tissue damage in the leg.

Many patients on ECMO systems will typically require diagnostics and therapeutic interventions, which are commonly facilitated by the placement of an introducer sheath 15, shown in FIG. 2, in the patient's artery. The introducer sheath 15 may also include a hub 16 with side arm 16a for venting air out of the system through venting tubing 17 by operation of a valve 18. The side port 5 of an ECMO arterial cannula 4 represents a potential access point to the ECMO circuit for vascular access. However, current vascular introducer sheaths 15 have no mechanism of interfacing with the side port 5. As is evident from FIG. 2, arterial sheaths 15 are too long and incompatible with the short right angle side port 5 provided in a cannula 4. They therefore offer no mechanism to negotiate the right angle presented by the side port 5, and no mechanism to direct a diagnostic or interventional wire or catheter in the appropriate direction (toward the patient rather than toward the ECMO pump) once inserted. Because insertion is not possible, introducer sheaths 15 provide no mechanism for establishing a hemostatic seal to the cannula 4, which would be needed for safe insertion of a wire or catheter. Attempts to insert a standard arterial sheath 15 into the side port 5 of a cannula 4 would result in uncontrolled bleeding around the sheath 15, inability to maintain the sheath 15 in appropriate position, kinking of the sheath 15, misdirection of intervention devices such as wires or catheters, and inability to pass wires or catheters altogether. For these reasons, currently available arterial sheaths are not amenable for insertion directly into a cannula.

SUMMARY OF THE INVENTION

The present invention is directed to adaptors, caps, cannulas, tube couplers, and systems including combinations thereof to permit the cannulas of an ECLS system, such as an ECMO circuit, to be used as an access point to gain endovascular entry. The various components provide the ability to interchangeably utilize the side port of a cannula not only for introduction of intervention devices, such as wires or catheters, into the cardiovascular system, but also for other purposes as well, such as establishing a secondary circuit for distal perfusion. Full occlusion of the side port is also made possible when the side port is not in use, to prevent blood stagnation and thrombus formation.

Specifically, the present invention is directed to a variety of adaptors that enable the use of an ECMO circuit as a vascular access point, and systems for vascular access that include such adaptors. These adaptors can interface with a standard cannulas currently used in ECLS systems, such as ECMO circuits, and provide an access point for intervention devices such as wires or catheters into the s system. The adaptors of the present invention include curved or straight shafts having an angle that can negotiate the right angle of a standard cannula side port and provide directionality to a wire or catheter inserted therein. A hemostatic membrane allows for insertion of the intervention device without back bleeding.

The present invention is also directed to a modified cannula with an angled side port. Such modified cannulas can be used with an adaptor as described herein. An occlusive cap is also provided that fully blocks the angled side port when vascular access or secondary perfusion is not needed. This occlusive cap prevents blood from stagnating in the angled side port, which could lead to thrombosis. Systems including the modified cannula, adaptor and occlusive cap are also described.

The present invention is further directed to a tube coupler that can be spliced into the tubing of an established or pre-existing ECLS system, including ECMO circuits. The coupler may have a standard right angle side port, or may have an angled side port with interchangeable adaptor and occlusive cap. A series of couplers may be inserted into the tubing of the bypass system, such as when a series of instruments or intervention devices must be inserted simultaneously for vascular access. Systems including the coupler with adaptors and/or occlusive caps, as previously described, are also included.

The adaptors, modified cannula, cap, coupler, and systems including the same, together with their particular features and advantages, will become more apparent from the following detailed description and with reference to the appended drawings.

DESCRIPTION OF THE DRAWINGS

FIG. 3 is a partial cross-section of one embodiment of an adaptor of the present invention shown inserted in an ECMO cannula.

FIG. 3A is a cross-section of the adaptor of FIG. 3.

FIG. 17D shows the coupler of FIG. 17C where the cap is removed, in preparation for direct access.

FIG. 17E shows the coupler of FIG. 17D where an adaptor is placed in the side port of the modified cannula for direct access.

FIG. 17F shows the coupler and adaptor of FIG. 17E in which direct access of an insertion device to the ECMO system is achieved through the adaptor and tubing connector.

FIG. 18 shows another embodiment of the tube coupler system where multiple couplers are serially spliced into the same bypass tubing and each provides endovascular access for a different insertion device.

FIG. 19 shows still another embodiment of the tube coupler system in which a single coupler includes a plurality of access ports, where each access port permits entry of a different insertion device for endovascular access.

Like reference numerals refer to like parts throughout the several views of the drawings.

DETAILED DESCRIPTION

Figure 1:
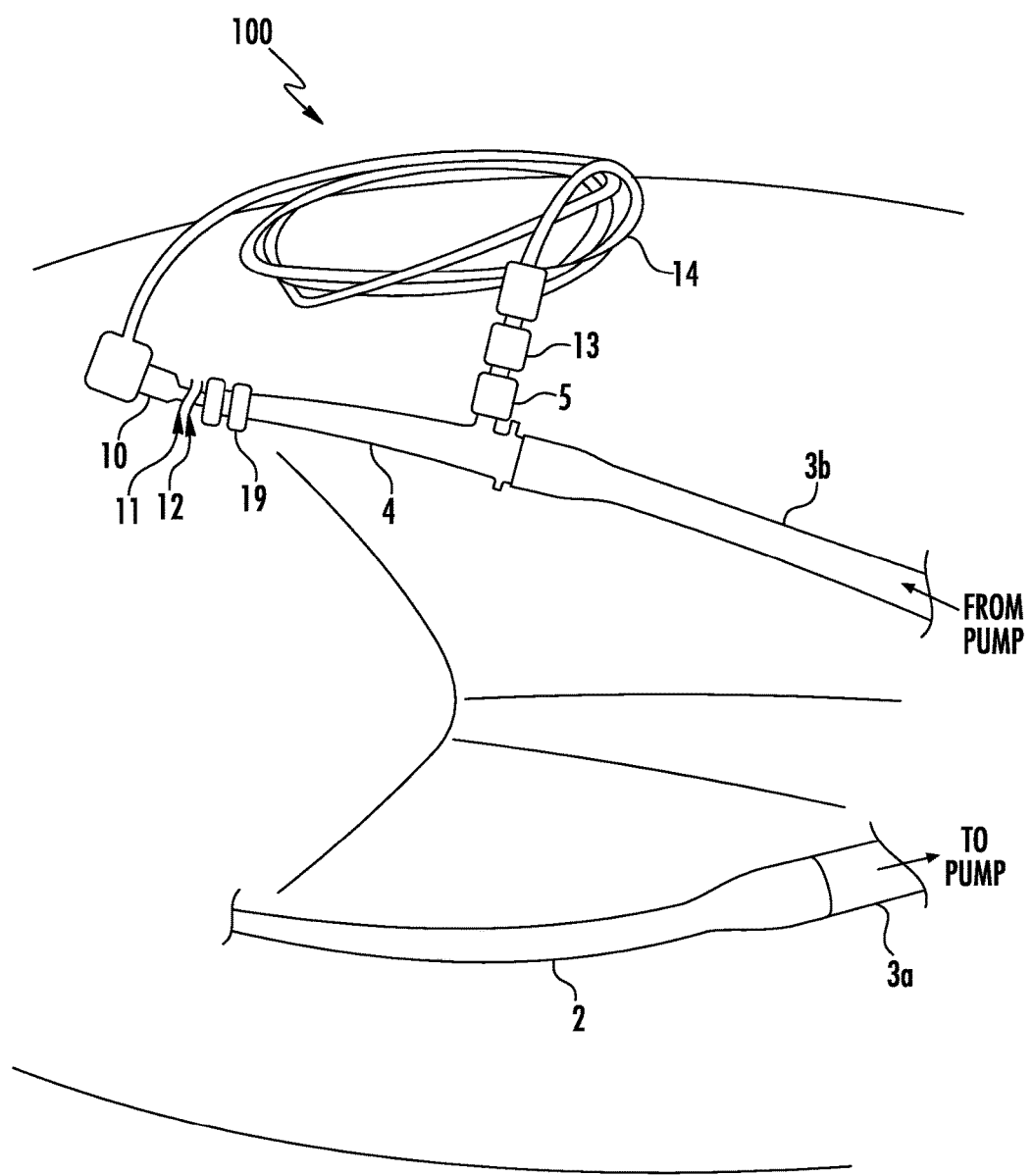
FIG. 1 is a diagram of a typical ECMO system of the prior art.
Figure 2:
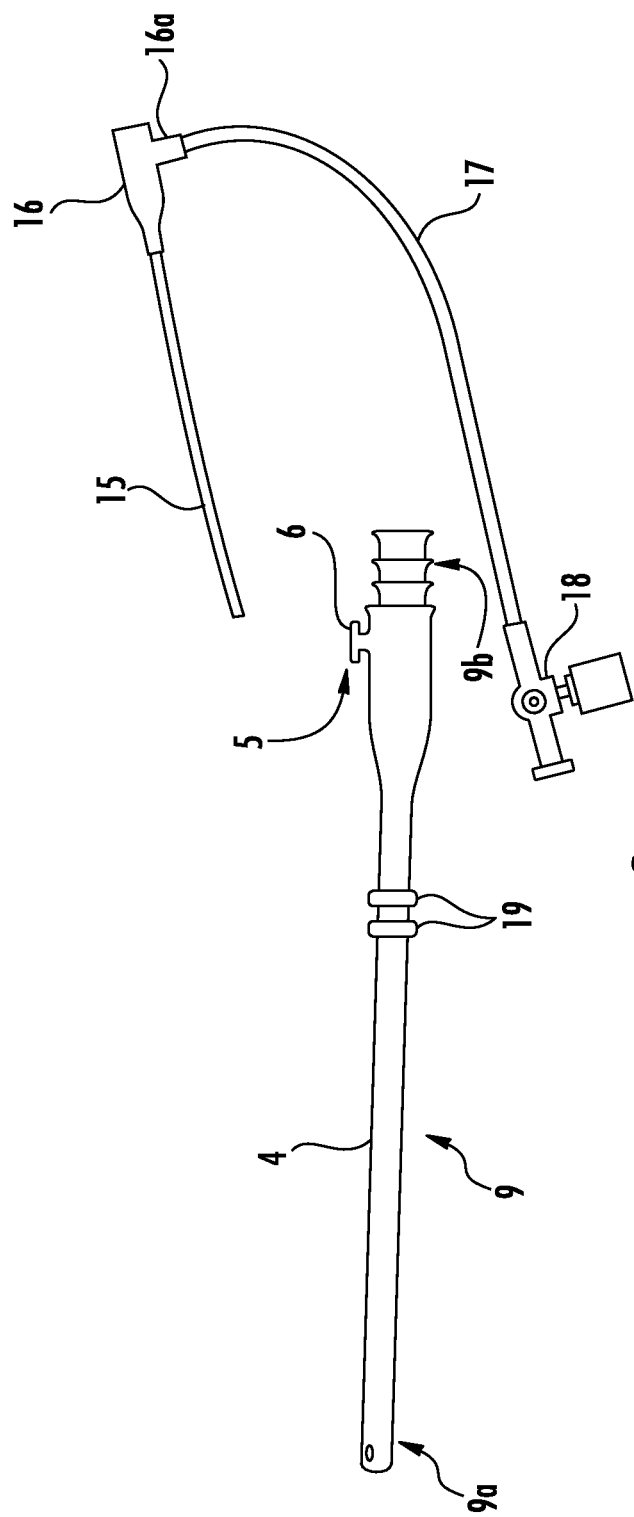
FIG. 2 is a diagram demonstrating the difficulties of direct access to an ECMO cannula.

As shown in the accompanying drawings, the present invention is directed to devices, such as adaptors, cannulas, tubing, and connectors that enable the use of an ECLS circuit, such as ECMO, as a vascular access point. The devices and systems enable not only vascular access for an intervention device, such as a wire, catheter or the like, but also provide full occlusion of the side port of the ECMO cannula when not in use. They are interchangeable with each other depending on whether vascular access is desired or not, and are further interchangeable with tubing connectors for secondary circuits, such as to establish secondary perfusion to an ipsilateral limb. This level of accessibility and interchangeability of components with a side port of a long-term use cannula has not been seen before. Further, the need to fully occlude the side port when not in use is of extreme importance in long-term systems, such as ECLS circuits, because of the increased potential for thrombus formation. The present invention addresses all of these needs not seen heretofor.

Although described here in the context of an ECMO system, it should be understood that the adaptors, cannulas, cap, tubing, couplers and systems of the present invention may be used with any appropriate cannulation or ECLS system, and is not limited to vascular applications. In addition, the devices and systems described herein can be used with bypass systems, such as a cardiopulmonary bypass circuit, for temporary support such as during an open heart operation. The inventions described herein may be more preferably used with longer term support circuits, such as those in use over 6 hours or more. In addition, the terms "subject" and "patient" may be used interchangeably and refer to the individual who is on bypass in which intracorporeal access is desired.

Adaptors for Standard Cannulas

As seen in FIGS. 3-5B, one aspect of the invention includes a variety of adaptors 30 designed for use with standard ECMO arterial cannulas 4 having a right angle side port 5 as an access point. These adaptors 30 can successfully navigate or circumvent the 90° turn of the side port 5 of an arterial or in-flow cannula 4 without kinking or damage. They therefore permit access to the cannula lumen 7, without obstructing the lumen, for access to the vascular system through the cannula 4. Accordingly, the adaptor 30 may be used instead of an introducer sheath 15 to access the vascular system, and enables access to the vascular system through the ECMO circuit without further percutaneous action.

As depicted in FIG. 3, the adaptor 30 includes a body 32 that acts as a hub for the remaining components of the adaptor 30, and may be manipulated by an operator or user during insertion. The body 32 is preferably made of a medical-grade plastic or other suitable material for medical use, and may be rigid. In some embodiments, the body 32 may include a side arm 37 that can be used for venting and otherwise removing air from the system, described in greater detail below.

The adaptor 30 also includes a shaft 33 that extends from one end of the body 32. In at least one embodiment, the shaft 33 may extend at least partially into the body 32 on one end, and extends away from the body 32 on the opposite end. The shaft 33 may include an elongate structure dimensioned to be inserted and pass through the side port 5 of a cannula 4, as shown in FIG. 3A. For instance, the shaft 33 may have a circular or tubular configuration, and a diameter that corresponds to, or is smaller than, the inner diameter of the side port 5. Accordingly, the shaft 33 may fit inside the side port 5, and may provide a snug fit in some embodiments. The shaft 33 is at least as long as the side port 5 of a cannula 4, and may extend into the cannula lumen 7. In some embodiments, the shaft 33 may extend to the wall of the cannula 4, but in at least one preferred embodiment the shaft 33 does not extend to the wall of the cannula 4. Regardless of the embodiment, however, the shaft 33 of the present adaptor 30 is shorter in length than that of a standard introducer sheath 15. The shorter length of the sheath 33 facilitates the navigation of the right angle side port 5 (discussed below) and prevents kinking of the shaft 33 when inserted into the side port 5.

The shaft 33 may be made of a semi-flexible plastic material, such as fluorinated ethylene polypropylene or polyethet block amide plastics used in endovascular and other intervention systems, or other suitable medical-grade plastics and materials. Such a semi-flexible material provides sufficient rigidity to maintain its shape for directional guiding of a wire or catheter, but is flexible enough to bend or flex slightly as needed during the insertion process and to prevent damage to the shaft 33 upon the introduction of a medical device therein. The body 32 of the adaptor 30 may be made of a similar semi-flexible material as the shaft 33, or may be made of more rigid material than the shaft 33.

Figure 4A:
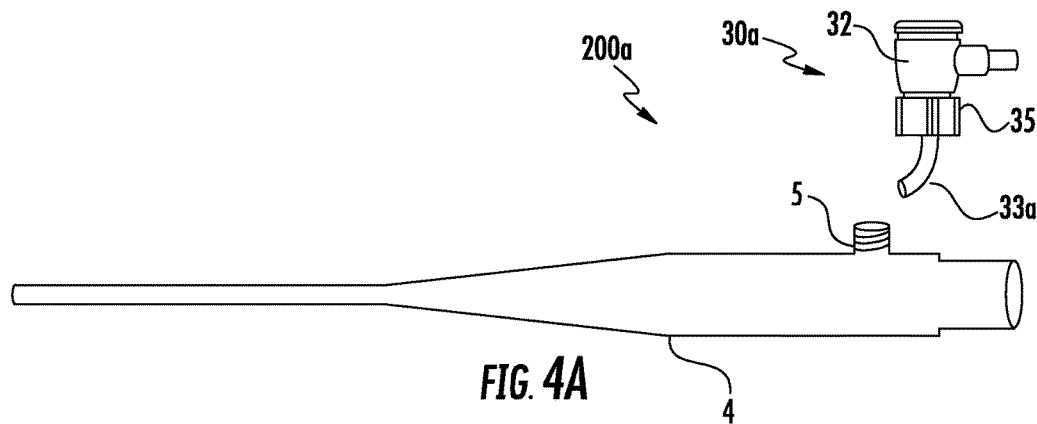
FIG. 4A shows the adaptor of FIG. 3 prior to insertion into an ECMO cannula.
Figure 4B:
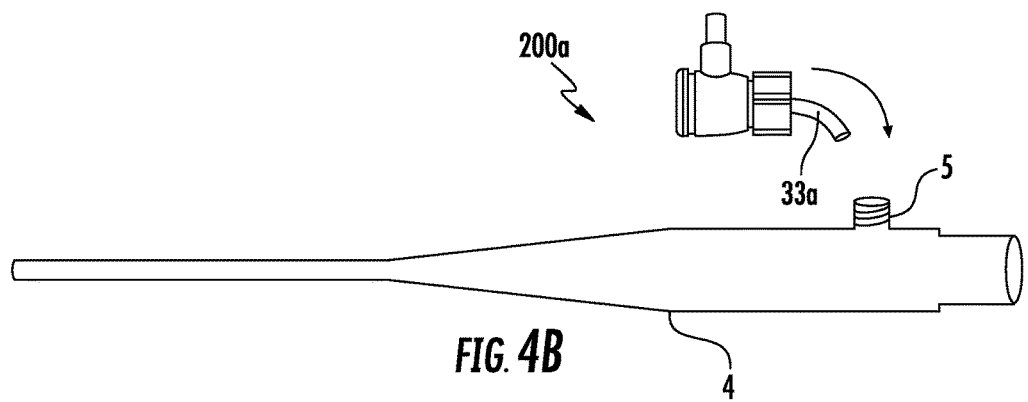
FIG. 4B shows the adaptor of FIG. 4A being inserted into the ECMO cannula.
Figure 4C:
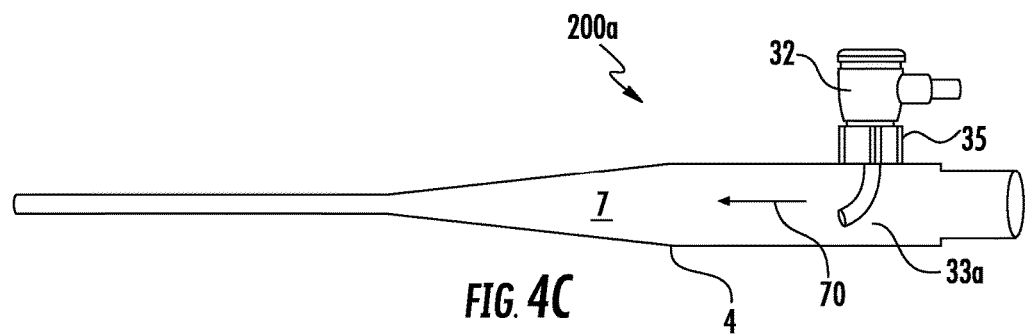
FIG. 4C shows the adaptor of FIG. 4A fully inserted into the ECMO cannula.

The shaft 33 may have a variety of configurations that enables modifying an angle of insertion of an intervention device, such as a wire or catheter, inserted into the adaptor 30 and directs the intervention device into the cannula lumen 7. For example, in at least one embodiment as depicted in FIGS. 3-4C, the shaft 33a is curved. The curved shape of the shaft 33a provides directionality to a medical device introduced therein, such as a wire or catheter. When positioned correctly, the curved shaft 33a reliably directs the wire or catheter introduced therein toward the patient's heart, rather than back in the direction of the ECMO system. The curved shaft 33a is long enough to extend into the cannula lumen 7 when inserted, but is also short enough in length to easily navigate the right angle of the side port 5 during insertion, as depicted through FIGS. 4A-4C. In FIG. 4A, an adaptor 30a having a curved shaft 33a is provided. To gain access to the cannula lumen 7, the distal opening of the curved shaft 33a is aligned with the opening of the side port 5, as shown in FIG. 4B. The distal end of the curved shaft 33a is inserted into the side port 5 of the cannula 4, and the adaptor 30a is rotated along the directional arrow shown in FIG. 4B until the curved shaft 33a is passed through the side port 5 and extends into the cannula lumen 7, as in FIG. 4C. Alignment of the curved shaft 33a and rotation of the adaptor 30a for insertion of the curved shaft 33a are performed so as to direct the opening of the curved shaft 33a toward the heart of the patient once fully inserted in the cannula 4, as depicted throughout FIGS. 4A-4C. The relatively short length of the curved shaft 33a, being slightly longer than the length of the side port 5, combined with the curvature of the shaft 33a, allows it to be rotated around the right angle of the side port 5 during insertion. It also prevents the shaft 33a from kinking at the inner wall of the cannula lumen 7, since in at least one embodiment the curved shaft 33a is not long enough to reach the opposite wall of the cannula lumen 7 during insertion. In some embodiments, the curved shaft 33a may be long enough to reach the opposite wall of the cannula lumen 7 during insertion, but in these embodiments the semi-flexible material of the curved shaft 33a allows it to flex and deflect off of the cannula wall, and resiliently keep its curved shape. Once the adaptor 30a is in place, as in FIG. 4C, a connector 35 can be tightened to selectively and releasable secure the adaptor 30a to the cannula 4, thereby securing the adaptor in place and preventing bleeding around it.

Figure 5A:
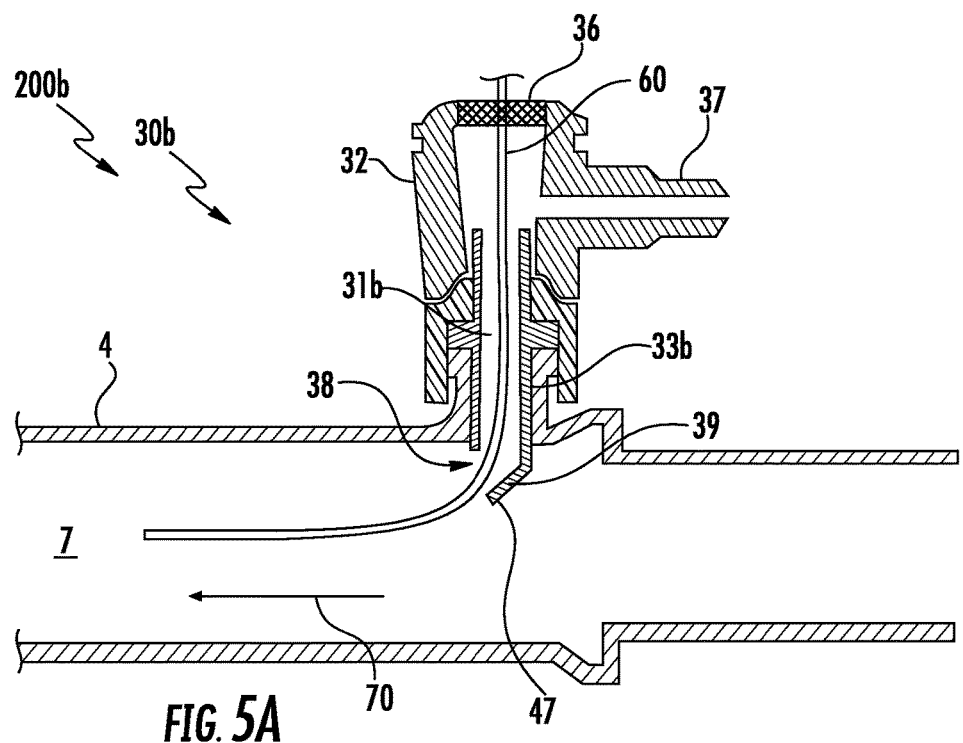
FIG. 5A is a cross-section of a second embodiment of an adaptor of the present invention.

In other embodiments, as in FIG. 5A, the shaft 33b has a straight configuration and extends substantially linearly from the body 32 of the adaptor 30b. In such embodiments, the distal end of the shaft 33b opposite of the body 32 includes a deflector 39 that protrudes or extends from an interior wall of the shaft 33b at an angle, thereby creating an angled surface for upon which a wire, catheter or other medical device inserted through the adaptor 30b may be deflected in a gentle curve to direct it into the cannula lumen 7. Accordingly, the deflector 39 changes the angle of the intervention device 60 from the initial angle of insertion to a different angle that directs the intervention device 60 into the cannula lumen 7. The deflector 39 may be made of the same semi-flexible material as the rest of the shaft 33b, as discussed previously, or may be made of a slightly more rigid material that resists flexing when pressure is applied, so as to direct an intervention device 60, such as a wire or catheter, appropriately and not lose its shape. As used herein, an intervention device 60 may be any diagnostic and therapeutic device used in medical procedures, and is not limited to wires or catheters. In some embodiments, the deflector 39 is made of a hard medical-grade plastic, such as polycarbonate or nylon, although other suitably rigid materials are also contemplated. In further embodiments, the entire shaft 33b, c and deflector 39 may be made of a hard plastic, polycbarbonate or nylon, or other rigid material. In some embodiments, as in FIG. 5A, the deflector 39 may be at the terminal end 47 of a straight shaft 33b, such that the shaft 33b has an angled end.

Figure 5B:
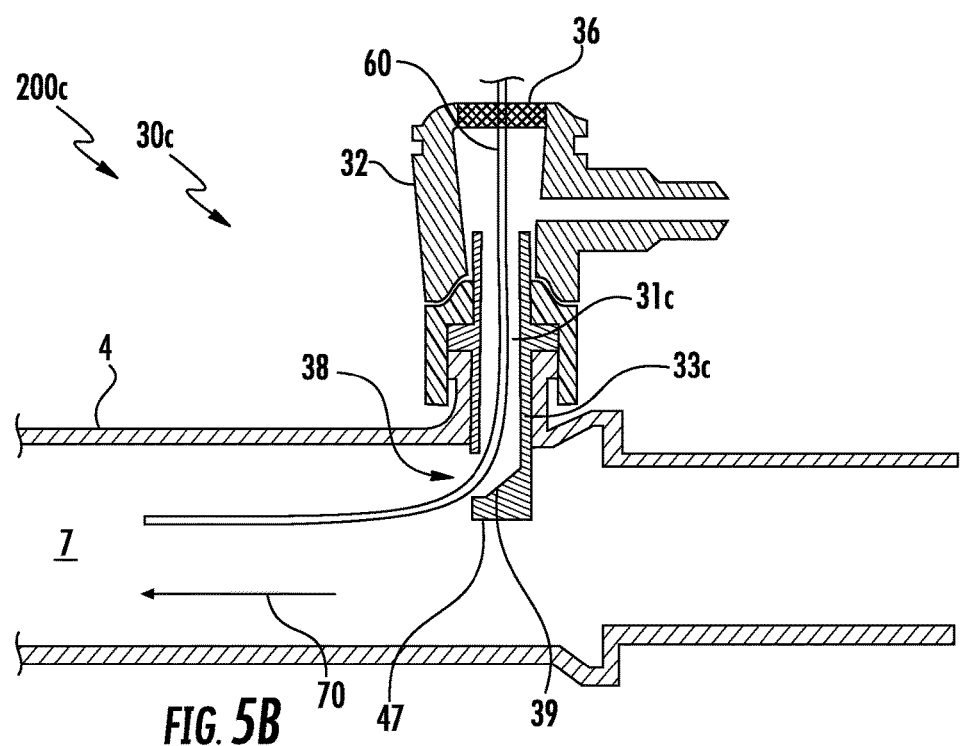
FIG. 5B is a cross-section of a third embodiment of an adaptor of the present invention.

In other embodiments, as in FIG. 5B, the straight shaft 33c may include a deflector 39 as before, but has a flat or straight terminal end 47 outer end. In these embodiments having a straight shaft 33b, c and a deflector 39, the shaft 33b, c may have an opening 38 at the side at the terminal end 47. Accordingly, the opening 38 is facing or pointed in the direction of the patient's heart, so as to appropriately direct a wire or catheter exiting from the shaft 33b, c. Additionally, the straight shaft 33b, c is longer in length than the side port 5, but is shorter than the distance to the opposite wall of the cannula 4. Accordingly, the right angle side port 5 does not pose a navigational risk in these straight shaft 33b, c embodiments, since the straight shaft 33b, c easily conforms to the straight channel 8 of the side port 5, and the internal deflector 39 creates the required angular change to direct an inserted wire or catheter toward the patient's heart.

Regardless of the particular configuration, the shaft 33 provides access for an intervention device 60 to the cannula lumen 7, and modifies the angle of insertion of the intervention device 60 and directs the intervention device 60 into the cannula lumen 7. Specifically, as seen in FIGS. 3A, 5A and 5B, the cannula lumen 7 has an axial flow path 70 of fluid (such as blood from an ECMO system) being directed through it. The shaft 33 of the adaptor 30 changes the direction of the intervention device 60 upon insertion and directs it not only into the cannula lumen 7, but specifically in the direction of, or consistent with, the axial flow path 70 of the cannula lumen 7. In at least one embodiment, this is toward the patient's heart, for cardiopulmonary intervention.

The shaft 33, and with reference to FIGS. 3A, 5A and 5B, may include a flange 34 that has a wider diameter than the remainder of the shaft 33. For example, the flange 34 may be circumferentially disposed around the shaft 33 and extend radially away from the shaft 33. The flange 34 is dimensioned to correspond with and abut a terminal lip 6 at the outermost edge of the side port 5 when the adaptor 30 is fitted on the side port 5. In this manner, the flange 34 may limit how far the shaft 33 may enter the side port 5 and cannula lumen 7.

The adaptor 30 may further include a connector 35, as shown in FIGS. 3A, 5A and 5B. The connector 35 is a fitting that removably secures the adaptor 30 to the side port 5 of the cannula 4. The connector 35 may be any suitable fitting for selectively releasable connection, such as a snap fitting, or a Luer connector that connects by screw action through a series of threads on the inside of the connector 35. These threads may interact with the lip 6 of the side port 5, such that as the connector 35 is turned or rotated about the side port 5, the lip 6 engages and is moved through the threads of the connector 35. In at least one embodiment, the connector 35 is a floating Luer connector that rotates independently of the remainder of the adaptor 30, such as the shaft 33. Such floating connector 35 may be preferable in embodiments where maintaining the direction or alignment of the opening 38 of the shaft 33 within the cannula lumen 7 is important, as in FIGS. 3-5B. In other embodiments, as when the orientation or direction of the shaft 33 is not critical after insertion, as in FIGS. 6 and 9-10, the connector 35 may be secured to and/or rotate with the adaptor 30 or shaft 33. In such embodiments, the connector 35 may be integrated into the adaptor 30, such as in the body 32 of the adaptor 30.

In at least one embodiment, the flange 34 of the shaft 33 may act as a washer between the connector 35 and the lip 6 of the side port 5, forming a seal when the connector 35 is tightened down onto the side port 5. Further, in some embodiments, the body 32 may include a cavity 49 on the underside which is correspondingly shaped to the connector 35, such that at least a portion of the connector 35 may be inserted into the cavity 49 of the body 32, as seen in FIG. 3A for example.

The adaptor 30 also includes an adaptor lumen 31 extending through and connecting the interior of the body 32 and shaft 33, shown in FIGS. 3A, 5A and 5B. The adaptor lumen 31 provides a hollow interior through which an intervention device 60 such as a wire or catheter may be introduced. The adaptor lumen 31 may be a single lumen, or may be separate lumens of the body 32 and the shaft 33 that are continuous with one another. Accordingly, in some embodiments, the adaptor lumen 31a is curved through a curved shaft 33a, as in FIG. 3A. In other embodiments, the adaptor lumen 31b, $c$ is straight through a majority of its length, and is angled at the distal end of the shaft 33$b$, $c$.

The adaptor lumen 31 is in fluidic communication with the cannula lumen 7 when the adaptor 30 is in place. Specifically, the adaptor lumen 31 extends through the body 32 and shaft 33 of the adaptor 30, and ends at the opening 38 of the distal end of the shaft 33. Therefore, the adaptor lumen 31 provides exterior access to the cannula lumen 7 of the ECMO system, including the axial flow path 70 thereof. The adaptor lumen 31 may also be in fluidic communication with a passage 48 extending through a side arm 37 of the adaptor 30. In such embodiments, any air that may be present in the cannula lumen 7 and the adaptor lumen 31 may be removed by selective venting through the passage 48 of the side arm 37, such as by operation of a valve connected to the side arm 37 through vent tubing 17, as in FIG. 3A.

The adaptor lumen 31 is dimensioned to receive an intervention device 60 such as wires and catheters, which may be up to about 7 French in diameter, or greater in some embodiments. The flange 34 of the shaft 33 and the connector 35 form a hemostatic seal with the side port 5, as mentioned previously, so that blood flowing through the ECMO system will not be lost during vascular access.

Further, the adaptor 30 may include a membrane 36 opposite of the shaft 33 through which a wire, catheter or other suitable diagnostic, therapeutic or other medical intervention device 60 may be passed to enter the adaptor 30 and gain access to the ECMO system and vascular system. In at least one embodiment, the membrane 36 is a hemostatic diaphragm, such as a silicone or other soft biocompatible plastic disc with a perforating slit(s) for access, as is used in insertion sheaths 15. As shown in FIGS. 3A, 5A and 5B, the membrane 36 is disposed in the body 32 of the adaptor 30 and spans the distance between the edge of the adaptor lumen 31 and the outer edge or exterior of the body 32. In other embodiments, the membrane 36 is coextensive with a top surface of the adaptor 30, as in FIGS. 3A, 5A and 5B. In other embodiments, the top surface of the adaptor 30 may not be uniformly flat, but may recess in, as in FIG. 9. Here, the membrane 36 spans from the adaptor lumen 31 to the outer edge of the body 32, which is the recessed portion. Regardless of configuration, the membrane 36 allows access to the adaptor lumen 31 while maintaining hemostatic conditions and preventing back bleeding upon insertion of an intervention device 60 therein.

The invention also includes various systems for vascular access 200. Each system 200 includes a cannula 4 and an adaptor 30 as described herein. For instance, at least one embodiment of a vascular access system 200$a$ includes a cannula 4 and an adaptor 30$a$ having a curved shaft 33$a$, as in FIG. 3A. In at least one other embodiment, the vascular access system 200$b$ includes a cannula 4 and an adaptor 30$b$ having a straight shaft 33$d$ terminating in an angled deflector 39, as in FIG. 5A. In at least one other embodiment, the vascular access system 200$c$ includes a cannula 4 and an adaptor 30$c$ having a straight shaft 33$c$ and a flat terminal end, with an internal deflector 39, as in FIG. 5B. These are just a few illustrative examples, and are not intended to be limiting.

Modified Cannula, Adaptor and Occlusive Cap

Figure 6:
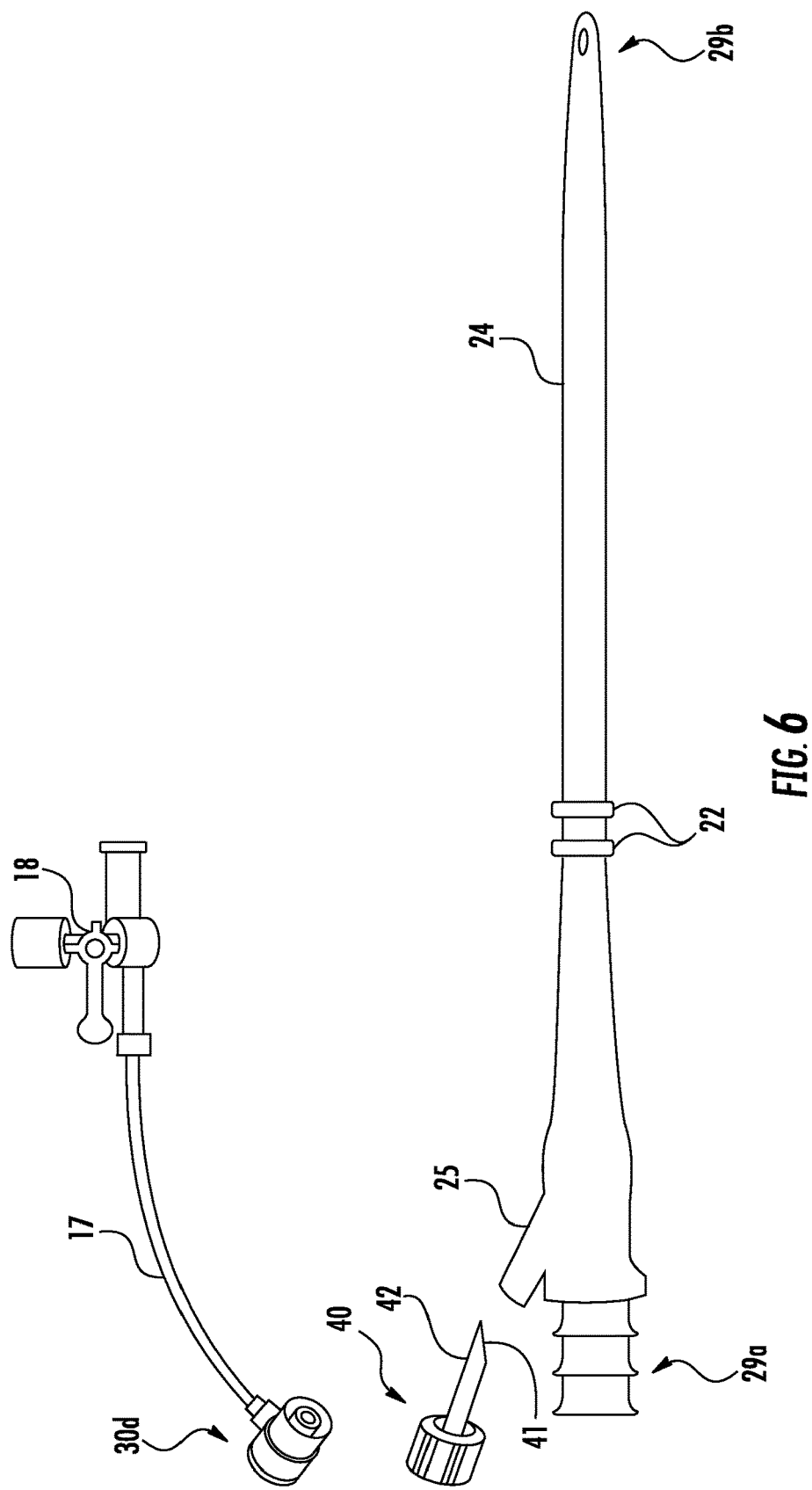
FIG. 6 shows a modified ECMO cannula, cap and adaptor of the present invention.
Figure 7:
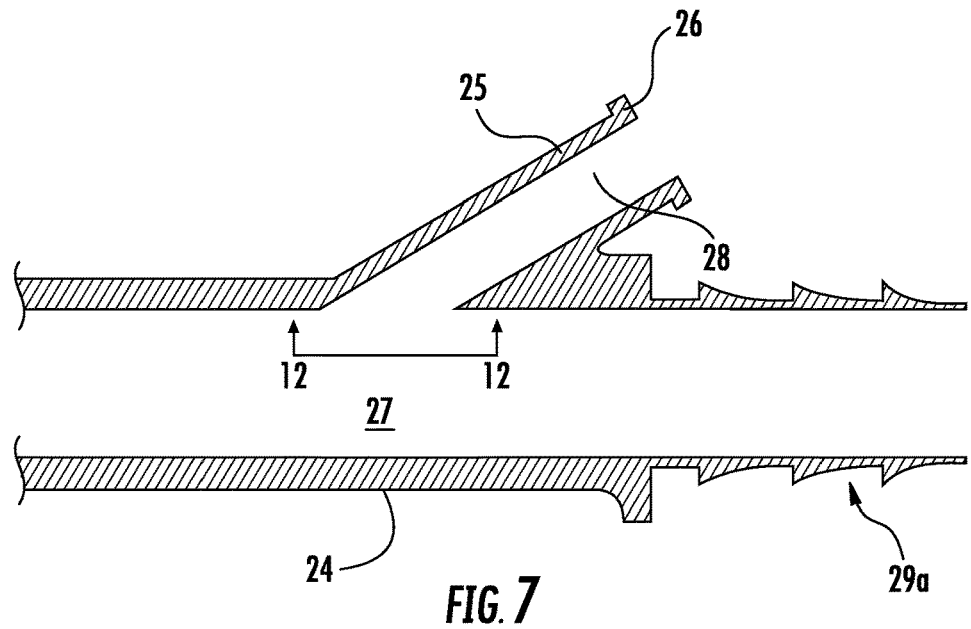
FIG. 7 is a cross-section of the modified ECMO cannula of FIG. 6.

Turning now to FIGS. 6-14, the present invention is also directed to a modified cannula 24 that can be used in an ECLS system in place of a standard arterial cannula 4, such as an ECMO vascular cannula. The modified cannula 24 is made of a flexible medical-grade plastic, silicon, or polymer material, or other material suitable for insertion and residence in a patient. As depicted in FIGS. 6 and 7, the modified cannula 24 includes an elongate portion 29 extending between a proximal end 29$a$ and an opposite distal end 29$b$. The proximal end 29$a$ is positioned closest to the pump of the bypass system, and has an opening at its terminal end and a diameter sized to receive and form a tight seal with the bypass tubing 3$b$ around its perimeter. For example, such bypass tubing 3$b$ may be ⅜ inch to ½ inch in diameter, and the proximal end 29$a$ may have a diameter ranging from 6 to 51 French depending on the particular application and whether it is used on an adult, child or infant. In some embodiments, the proximal end 29$a$ includes ribs, barbs, serrations, or other frictional elements that engage the interior of the bypass tubing 3$b$ upon insertion and maintains or facilitates a tight seal with the tubing 3$b$. Accordingly, when attached to the bypass tubing 3$b$, the proximal end 29$a$ of the modified cannula 24 receives blood from the ECLS system, such as an ECMO system.

The opposite distal end 29$b$ of the modified cannula 24 is dimensioned to be inserted into a subject or patient, such as a blood vessel for vascular access, and more in particular an artery, such as the femoral artery or aorta, or a vein, such as the femoral vein or internal jugular vein. For instance, the distal end 29$b$ may have a diameter ranging from 14 to 22 French, although smaller or larger sizes are also contemplated. The distal end 29$b$ is preferably narrower than the proximal end 29$a$, as in FIGS. 6 and 7. In other embodiments, however, the distal end 29$b$ and proximal end 29$a$ may have the same diameter, or the distal end 29$b$ may have a larger diameter than the proximal end 29$a$. The distal end 29$b$ is also made of a flexible medical-grade plastic, silicon, or polymer material, or other suitable material, so as to avoid damaging or puncturing the blood vessel. The distal end 29$b$ may also include an opening(s) at or near the distal tip to allow reinfusion of blood into the surrounding blood vessel from the modified cannula 24.

Between the proximal end 29$a$ and distal end 29$b$, the modified cannula 24 may include a depth guide(s) 22 located along the length of the elongate portion 29. The depth guide(s) 22 provide a visual indicator for a user, such as a medical practitioner, of how far to insert the distal end 29$b$ of the modified cannula 24 into the subject. For instance, in at least one embodiment, the distal end 29$b$ of the modified cannula 24 is inserted into the patient at an incision point until the depth guide(s) 22 reaches the incision. The depth guide(s) 22 therefore provides a maximum limit for insertion. In at least one embodiment, the depth guide 22 may be a collar or series of collars disposed circumferentially around the exterior of the elongate portion 29 of the modified cannula 24. In other embodiments, the depth guide 22 may be a marking or series of markings on or integrally formed in the wall of the modified cannula 24, such as printed on or engraved in the exterior surface of the modified cannula 24.

The modified cannula 24 also includes a modified cannula lumen 27 extending through the length of the modified cannula 24 from the opening at the proximal end 29$a$ to the opening at the distal end 29$b$. Accordingly, the modified cannula lumen 27 provides an axial flow path 70' through which fluid, such as blood, may pass during ECMO circulation. The modified cannula lumen 27 has a diameter similar to that of the modified cannula 24, and in at least one embodiment takes up a majority of the inner volume of the modified cannula 24.

As shown in FIGS. 6 and 7, the modified cannula 24 further includes an angled side port 25 that extends from the surface of the modified cannula 24. Notably, the angled side port 25 extends away from the surface at an angle, which may be any angle other than 90°. For instance, the angled side port 25 extends from the surface of the modified cannula 24 at an acute angle less than 90°, such as in the range of 10° to 40° from the modified cannula 24 wall in at least one embodiment. In another embodiment, the angle of the angled side port 25 is in the range of 25° to 35°. These are illustrative examples, and are non-limiting. For instance, depending on the perspective, the angled side port 25 could be considered to extend at an obtuse angle from the modified cannula 24.

The angled side port 25 terminates at a lip 26 having a wider diameter than the rest of the angled side port 25, so as to form an overhanging portion. The angled side port 25 may also have a thread to allow interaction with Luer connections or other counterthreads on the connector 35 of adaptors 30. The angled side port 25 also has an opening at the terminal end, and an angled side port channel 28 extending through the angled side port 25 in fluid communication with the opening on one end and the modified cannula lumen 27 on the opposite end. Accordingly, the angled side port 25 provides exterior access to the modified cannula lumen 27, and therefore to the vascular system for endovascular diagnostic and therapeutic procedures.

The angled side port 25 of the modified cannula 24 provides a number of benefits over the standard right angle side ports 5 of current vascular arterial cannulas 4. For instance, the angle of the angled side port 25 directs an incoming wire, catheter or other inserted medical device to more closely align with the modified cannula lumen 27 in a direction toward the heart of the patient. This facilitates the insertion of such a device without having to navigate around a right angle, as with standard cannulas 4, thereby preventing kinking and obstruction of the wire or catheter.

Cardiopulmonary bypass cannulas with an angled side arm or a Y-shape have been described in the prior art. However, these cannulas have several disadvantages that limit their utility in an ECMO system. For instance, when a typical bypass cannula is inserted into a vessel, it may occlude blood flow to distally located tissues. As shown in FIG. 1, when a cannula is inserted into the femoral artery, blood flow to the entire ipsilateral leg may be jeopardized. In order to prevent ischemia of distal tissue beds, the right angle side port 5 of a cannula 4 can be used to establish a secondary circuit 14 to direct a portion of the blood flow in the opposite direction to the cannula 4. Blood flow may be directed out of the right angle side port 5 of the cannula 4 and down the ipsilateral leg to separately perfuse the leg. Secondary circuits for distal perfusion are not always necessary, and may not be needed the entire time the patient is supported on the ECMO system, but they are frequently used. Thus, the ability to establish of a downstream flow circuit is an important option when using long-term bypass systems such as ECMO. However, cardiopulmonary bypass cannulas with angled side arm previously described in the prior art lacks the requisite structure to establish a connection for a secondary circuit 14 for distal perfusion.

In contrast, the modified cannula 24 with angled side port 25 of the present invention includes a lip 26 at the terminal end, as seen in FIG. 7. This lip 26 provides a surface on which a connector, such as a Luer connector, can be used to engage for secure yet selectively removable connection. Accordingly, a Luer connector commonly used as a secondary tubing connector 13, shown in FIG. 1, can engage the lip 26 of the angled side port 25 of the modified cannula 24, shown in FIG. 7, to establish a secondary circuit as previously described for distal perfusion. For example, the lip 26 of the angled side port 25 is dimensioned to fit within the grooves, threads, or tracks of a connector, such as a Luer connector having internal threading for connection by screwing action. Common cardiopulmonary bypass cannulas, even those with angled side arms, lack this structure. Although Luer connectors are described here as removably engaging the lip 26 of the angled side port 25, it should be appreciated that other types of connectors could also be used to removably engage the lip 26 for a secure connection, such as snap on connectors.

In addition, in an ECMO circuit, blood flow along the main lumen 7 of the cannula 4 is laminar. A typical angled side arm represents an arm with a blind end, since laminar flow does not penetrate the side arm. The lack of flow in the side arm creates a potential for stagnant blood to pool in the side arm, which may result in thrombus formation, particularly during periods of prolonged support on ECMO. If a thrombus forms and is later dislodged, it may result in devastating complications including stroke, myocardial infarction, ischemic bowel, or ischemia of other tissues. Therefore, known cardiopulmonary bypass cannulas with an angled side arm or a Y-shape cannot be used in ECMO systems. Further, many cardiopulmonary bypass cannulas with an angled side arm or a Y-shape have permanent valves located within the side arm. Such permanent valves may increase the risk of stagnant blood flow and thrombus formation. The angled side port 25 of the modified cannula 24 of the present invention lacks such permanent valves that would lead to stagnant blood flow and thrombus formation.

In addition, the angled side port 25 of the modified cannula 24 of the present invention is designed to coordinate with a specialized occlusive cap 40 for use when access to a secondary circuit 14 or endovascular access is not needed. Specifically, the occlusive cap 40 of the present invention is designed to fit inside the angled side port channel 28 of the angled side port 25 and occlude substantially all of the angled side port 25, such that blood does not flow into the angled side port 25 from the ECMO system when access is not needed. This prevents blood stagnation and potential thrombus formation, and is not available with known ECMO or cardiovascular bypass cannulas.

Figure 8:
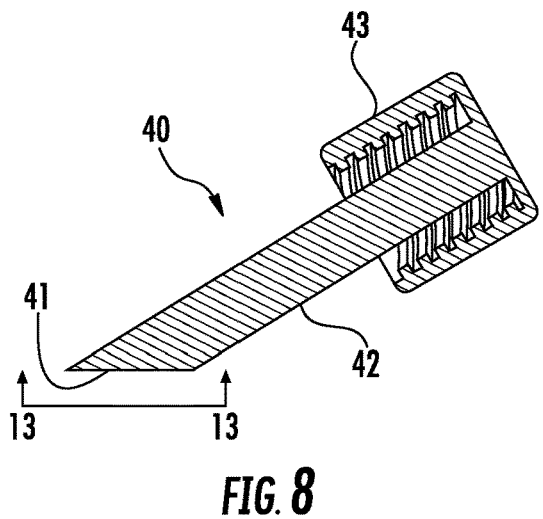
FIG. 8 is a cross-section of a modified cap of FIG. 6.
Figure 11:
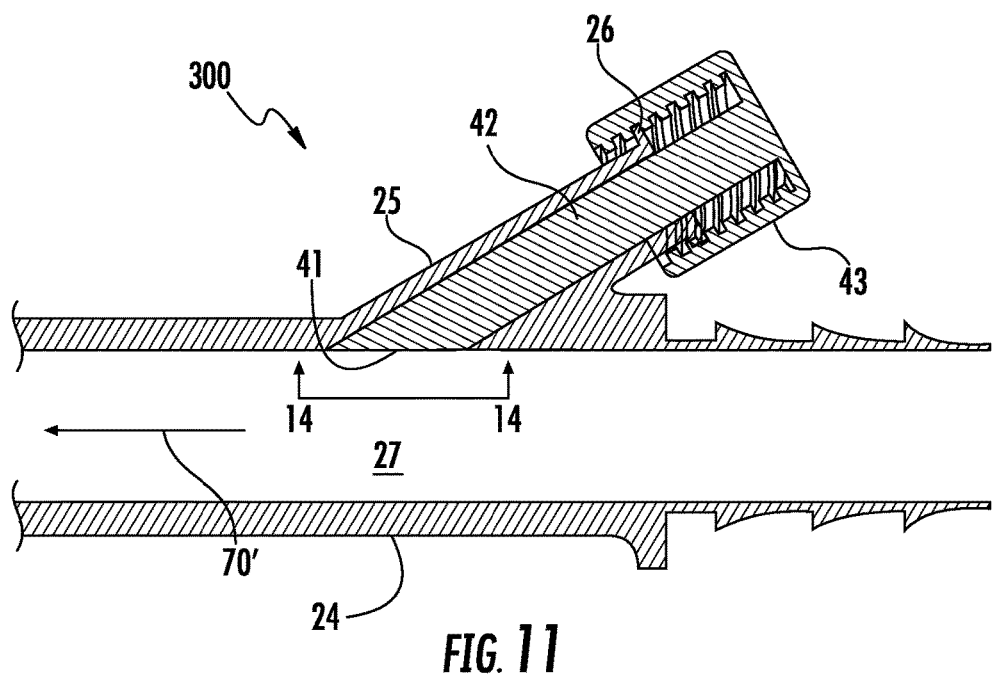
FIG. 11 is a cross-section showing the cap and modified ECMO cannula of FIG. 6.
Figure 12:
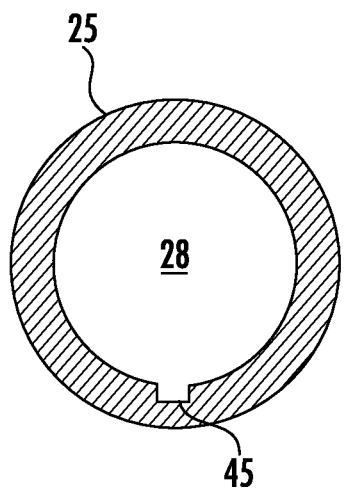
FIG. 12 is a cross-section of the sideport opening of one embodiment of the modified ECMO cannula of the present invention.

As seen in FIGS. 7, 8 and 11, at least a portion of the occlusive cap 40 is correspondingly dimensioned in size and shape to fit inside the angled side port channel 28 and provide a tight fit therein. Specifically, the occlusive cap 40 includes an occluding member 42 terminating in an occluding surface 41, as seen in FIGS. 8, 11, 13 and 14. The occluding surface 41 blocks the angled side port channel 28 and prevents blood from entering. It therefore prevents blood stagnation and potential thrombus formation. As depicted in the cross-section of FIG. 11 and the view along line 14-14 shown in FIG. 14, the edges of the occluding surface 41 are adjacent to and abut the interior surface of the angled side port channel 28, so as to form a tight fit therewith. In a preferred embodiment, as in FIG. 11, the occluding surface 41 is flush or coextensive with the wall of the modified cannula lumen 27, such that the occluding member 42 of the occlusive cap 40 does not extend into the modified cannula lumen 27 and laminar blood flow through the modified cannula lumen 27 is not disrupted. However, in some embodiments the occluding member 42 may extend into the modified cannula lumen 27, such as to ensure the angled side port channel 28 is entirely blocked.

Figure 13:
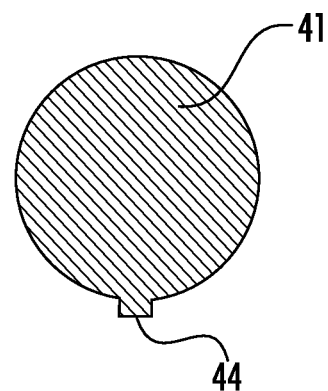
FIG. 13 is a cross-section of the occluding surface of one embodiment of the cap of the present invention.
Figure 14:
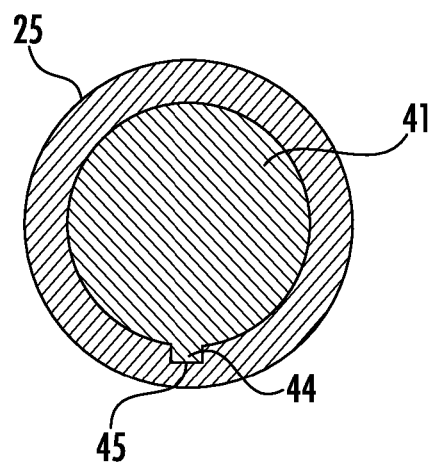
FIG. 14 is a cross-section of the occluding surface of the cap of FIG. 13 when inserted in the sideport of the modified ECMO cannula of FIG. 12.

In some embodiments, the occluding surface 41 may have a locking member 44, as shown in FIGS. 13 and 14. This locking member 44 is located along the perimeter of the occluding surface 41 and is correspondingly dimensioned with a receiver 45 located in the inner perimeter or edge of the angled side port 25, such as in the angled side port channel 28. As illustrated through FIGS. 12-14, the locking member 44 and receiver 45 correspondingly fit together to form a tight fit, but may also provide locking engagement for securely retaining the occluding surface 41 in the angled side port 25 in a particular orientation. This engagement may also be used to ensure the occlusive cap 40 is fully inserted and/or properly aligned within the angled side port channel 28 so that the occluding surface 41 is flush or fully coextensive with the wall of the modified cannula lumen 27, as the locking member 44 and corresponding receiver 45 may only interact and engage in a particular configuration. In at least the embodiment shown in FIGS. 12-14, the locking member 44 is an extension that extends from the perimeter of the occluding surface 41, and the receiver 45 is a recess formed in the angled side port 25 having a corresponding shape, contour and dimension to the locking member 44. However, it should be understood that in other embodiments, the locking member 44 may be located in the angled side port 25 and the receiver 45 may be located in the perimeter of the occluding surface 41. Similarly, the locking member 44 and receiver 45 may have any shape, dimension or contour permitted by the occluding surface 41 and angled side port 25, so long as they coordinate together. For example, the locking member 44 may be a keyed extension, the receiver 45 may be a rail or track, and either or both the locking member 44 and receiver 45 may include threading for coordinated interaction. These are just a few illustrative examples, and are not meant to be limiting.

In at least one embodiment, the occluding member 42 may have an elongate shape, such as a cylinder or shaft that extends at least a portion of the length of the occlusive cap 40. In some embodiments, the occluding member 42 extends the entire length of the occlusive cap 40. At least a portion of the occluding member 42 has a diameter that is substantially the same as or slightly smaller than the diameter of the angled side port channel 28. In one embodiment, the entire length of the occluding member 42 has a diameter corresponding to the diameter of the angled side port channel 28 of the modified cannula 24. In other embodiments, however, only a portion of the occluding member 42 has a diameter corresponding to the diameter of the angled side port channel 28. This portion may be located anywhere along the occluding member 42, such as at an end or anywhere along the length of the occluding member 42.

Regardless of the length and diameter of the occluding member 42, it terminates at the occluding surface 41 on one end, as depicted in FIG. 8. Therefore, the occluding member 42 may be at least as long as the angled side port channel 28 and the angled side port 25 in some embodiments. In a preferred embodiment, the occluding member 42 is the same length as the angled side port channel 28. In some embodiments, the width or diameter of the occluding member 42 is the same as that of the occluding surface 41. In other embodiments, the width or diameter of the occluding member 42 is less than that of the occluding surface 41, or may vary in its diameter over its length.

At the opposite end of the occluding member 42 from the occluding surface 41, the occlusive cap 40 may also include a cap connector 43, as shown in FIG. 8. The cap connector 43 selectively retains the occlusive cap 40 on the modified cannula side port 25 for selectively reversible securing. For instance, the cap connector 43 is dimensioned to removably engage the lip 26 of the angled side port 25 to secure the occlusive cap 40 in place upon insertion into the angled side port 25. The cap connector 43 may be shaped as a Luer connector, such as a floating or fixed Luer connector, and may include threads disposed along an inner surface for receiving the lip 26 of the angled side port 25. Of course, other forms of selectively reversible attachment are also contemplated, and are not limited to threaded engagement. The cap connector 43 may be integrally formed with the occlusive cap 40, as in FIG. 8, although in other embodiments it may be formed separately and attached to the occlusive cap 40, such as at the occluding member 42. The cap connector 43 allows the occlusive cap 40 to be secured to the angled side port 25 when the modified cannula 24 does not need to be accessed. However, it is selectively reversible to permit removal of the occlusive cap 40 for access to the modified cannula 24 through the angled side port 25, such as to establish a secondary circuit as previously discussed or to insert a wire, cannula or other medical device.

Accordingly, the occlusive cap 40 and modified cannula 24 described herein together form an occlusion system 300, as seen in FIG. 11. When the occlusive cap 40 is fully inserted in the angled side port 25 of the modified cannula 24, the laminar blood flow through the bypass system is substantially entirely occluded from the angled side port 25. This is important to prevent thrombus formation in long-term use systems such as ECLS.

When access to the modified cannula lumen 27 is desired, such as for the insertion of a wire or catheter or to establish a secondary circuit for distal perfusion, the occlusive cap 40 may be removed from the angled side port 25. The bypass tubing 3b may be clamped upstream of the modified cannula 24 prior to removal of the occlusive cap 40, such that blood flow through the system is temporarily interrupted. This prevents blood from seeping into the angled side port channel 28 upon removal of the occluding surface 41 and the occlusive cap 40. Once the occlusive cap 40 is removed, secondary circuit tubing may be connected to the angled side port 25 in a similar fashion as it would connect to a right angle side port 5. The clamp on the bypass tubing 3b may then be released, reestablishing the blood flow through the system, which now includes a secondary circuit for distal perfusion. On the other hand, if endovascular access is desired, such as through the insertion of a wire or catheter, an adaptor 30d may be attached to the angled side port 25 during temporary interruption of the ECMO system, as described below. After either is attached, the clamp may be removed and ECMO flows reinstituted.

Figure 9:
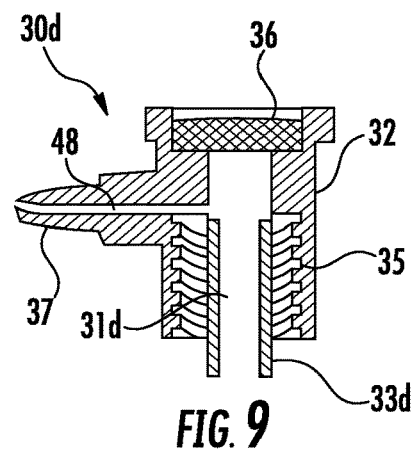
FIG. 9 is a cross-section of the adaptor of FIG. 6.
Figure 10:
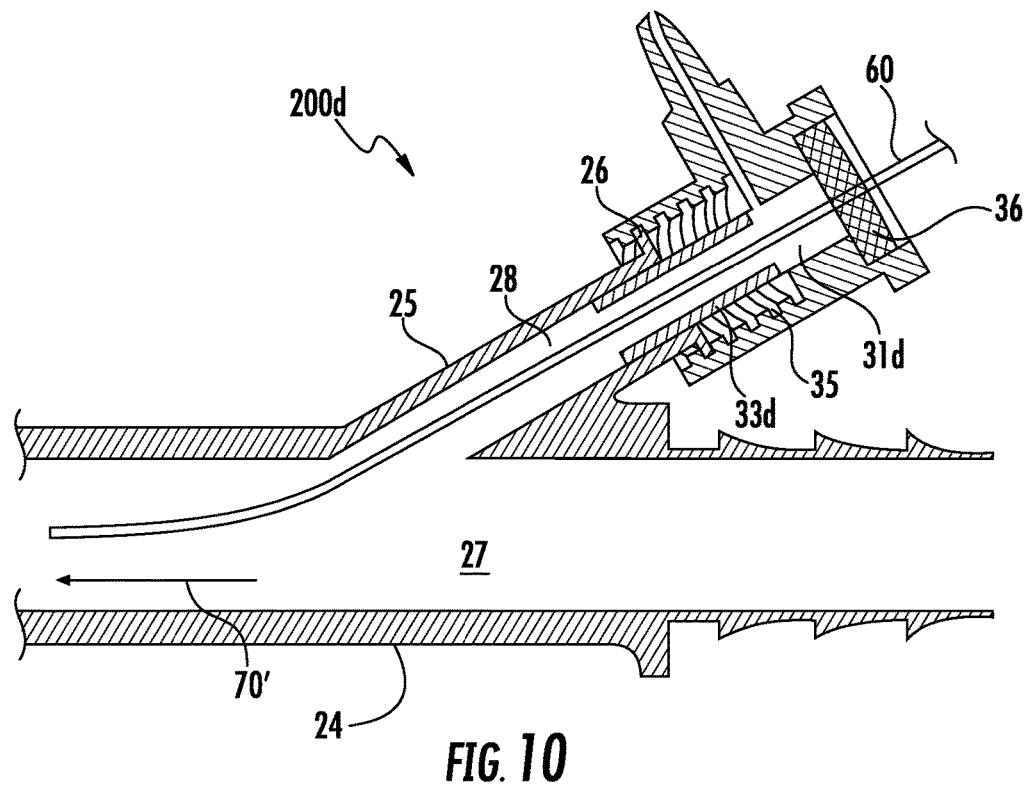
FIG. 10 is a cross-section showing the adaptor and modified ECMO cannula of FIG. 6.

The present invention also includes an adaptor 30d, as seen in FIGS. 9 and 10. Because the adaptor 30d and occlusive occlusive cap 40 are interchangeable, the adaptor 30d may also be considered an insertion cap, and the terms are used interchangeably herein. The adaptor/insertion cap 30d includes a body 32, a membrane 36 for hemostatic access, and an adaptor or insertion lumen 31d extending from the membrane 36 and through the body 32, similar to those of the previously described adaptors 30a, b, c. However, the adaptor/insertion cap 30d is used with the angled side port 25 of the modified cannula 24 to permit exterior access to the modified cannula lumen 27, and thus the ECMO system for endovascular entry. The adaptor 30d need not provide directionality for the insertion of a wire or catheter since that function is already provided by the angle of the angled side port 25. Therefore, in at least one embodiment the adaptor/insertion cap 30d may not include a shaft 33 or other structure that extends into the angled side port channel 28 of the angled side port 25. In such embodiments, the adaptor or insertion lumen 31d is in fluid communication with the angled side port channel 28 when the adaptor/insertion cap 30d is connected to the angled side port 25. In other embodiments, as in FIGS. 9 and 10, the adaptor/insertion cap 30d includes a shaft 33d. The adaptor lumen 31d is sized to coordinate with the angled side port channel 28, and may be the same or similar diameter as the angle side port channel 28. The adaptor lumen 31d is sized to allow the passage of wires, catheters and other medical devices that may be used for cardiovascular interventions, such as 7 French or greater. Accordingly, an intervention device 60 can be passed through the hemostatic membrane 36 and enter the adaptor lumen 31d, pass through the adaptor lumen 31d directly into the angled side port channel 28, and on into the modified cannula lumen 27.

In other embodiments, the adaptor/insertion cap 30d may include a shaft 33d that is straight and may be shorter than the shafts 33a, b, c of the previously discussed adaptors 30a, b, c. When present, the shaft 33d may extend into at least a portion of the angled side port channel 28, or even into the modified cannula lumen 27. Accordingly, in some embodiments, the shaft 33d may be 7 French in diameter or greater, such as to permit the passage of intervention devices such as medical devices for cardiovascular intervention, but still fits within the angled side port channel 28. The shaft 33d may be integrally formed in the body 32 of the adaptor/insertion cap 30d, or may attach to the body 32 such as by secure attachment as with adhesive or molding.

The adaptor/insertion cap 30d may attach to the exterior of the angled side port 25, such as by engaging the lip 26 of the angled side port 25 with a connector 35 as previously described. Because directionality is not a function of the adaptor 30d with an angled side port 25, the connector 35 of the adaptor 30d may be fixed, formed in or integral with the body 32 of the adaptor 30d, as shown in FIG. 9. Thus, when the adaptor 30d is attached to the angled side port 25, the entire body 32 may be rotated around the angled side port 25, to provide a secure, selectively reversible connection such as by screw-type action of threading of the connector 35 with the lip 26 of the angled side port 25. Of course, in other embodiments, the connector 35 may be a floating Luer connector as previously described, or a retaining structure that permits the adaptor 30d to slide or snap onto the lip 26 of the angled side port 25, whereby the lip 26 retains the adaptor/insertion cap 30d in place.

Accordingly, the present invention also include another embodiment of a vascular access system 200d including a modified cannula 24 having an angled side port 25 and an adaptor/insertion cap 30d having a shorter shaft 33d as described above, such as depicted in FIG. 10. The adaptor/insertion cap 30d, and specifically the shaft 33d, provides exterior access of an intervention device 60 to the modified cannula lumen 27 so as to change the angle of insertion of the insertion device 60 to be inline with or consistent with the axial flow path 70'. In addition, the cannula may not be limited to one side port. For example the cannula may have one or more angled side ports, right angle side ports, or some combination thereof.

Tube Coupler

In addition, the present invention also includes a tube coupler 50 that may be inserted or spliced into ECMO or any bypass tubing to provide additional side ports 5, 25 for endovascular access. For instance, some patients arrive at a medical facility with an ECMO or other ECLS system already in place, in which the arterial cannula 4 may not have a side port 5 for endovascular access, and yet endovascular access may become necessary at some point while the patient is on support. In other instances, the arterial cannula 4 of the ECLS system may only have a single side port 5, but multiple devices (such as wires, catheters, etc.) may be needed to be inserted at the same time for simultaneous endovascular access, such as for coordinated actions to perform a medical procedure. The side port 5 and its hemostatic membrane 36 may allow only one device through at a time, in order to maintain the hemostatic seal and prevent back bleeding. Since multiple couplers could be inserted into an ECLS circuit, the tube coupler 50 of the present invention therefore provides a way to introduce additional side ports 5, 25 for additional points of access to the ECMO or other ECLS system.

Figure 15:
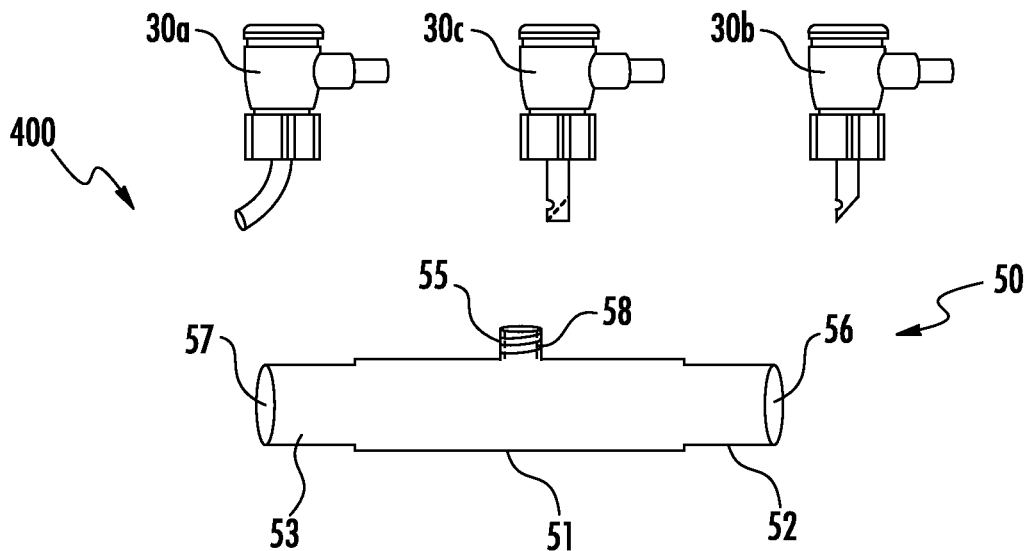
FIG. 15 is one embodiment of a system using one version of a tubing connector with various adaptors of the present invention.

As seen in FIG. 15, the tube coupler 50 includes a first end 52 having a first end opening 56, and an opposite second end 53 with a second end opening 57, and a coupler body 51 disposed there between. The first and second ends 52, 53 are sized and shaped to accommodate and selectively matingly fit independent or separate sections of bypass tubing 3b, such as ECMO tubing, on an arterial side of the bypass system. The first and second ends 52, 53 may be slightly narrower in diameter than the coupler body 51 of the tube coupler 50, and in some embodiments may taper slightly, to allow a tight hemostatic seal when the tubing 3b is attached. In some embodiments, the first and second ends 52, 53 may have ribs, barbs, serrations, beveling, or other frictional structure to promote a tight seal and retention of the ECMO or bypass tubing 3b. Accordingly, the first and second ends 52, 53 may have a similar structure to the proximal end 9a of a standard arterial cannula 4, as discussed previously, although it is not required. In some embodiments, the first and second ends 52, 53 have the same diameters and structural features. In other embodiments, the first and second ends 52, 53 may have different diameters and structural features from one another.

The coupler body 51 extends between the first and second ends 52, 53 and may have an elongate length. In a preferred embodiment, the coupler body 51 may be a cylinder, although other shapes and configurations are contemplated. A coupler lumen 54 extends through at least a portion of the tube coupler 50 at the coupler body 51. In at least one embodiment, the coupler lumen 54 extends from the first end opening 56 to the second end opening 57 and through the coupler body 51 such that the coupler lumen 54 provides an axial flow path 70' for fluid such as blood to flow entirely through the tube coupler 50 when inserted in a bypass system. The coupler lumen 54 thus allows the tube coupler 50 to be inserted into, and become part of, an established bypass system and permit the continued functioning of the bypass system.

The tube coupler 50 further includes a access port 55 located along the coupler body 51. The access port 55 may be a right angle side port 5, as shown in FIG. 15, such as is provided on commercially available arterial cannulas 4 as described above. Specifically, the access port 55 includes a length that extends away from the coupler body 51 of the tube coupler 50. The access port 55 defines a access port channel 58 extending through at least a portion of the interior of the access port 55, which is in fluid communication with the coupler lumen 54 at one end, and has an opening at the other end for receiving the shaft 33 of an adaptor 30 as previously described, such as adaptors 30a, b, c. Accordingly, the access port channel 58 provides exterior access to the coupler lumen 54 such that a wire, catheter or other intervention device 60 may be inserted through a hemostatic membrane 36 within such adaptor 30, as previously described, and be inserted into the access port channel 58 of the tube coupler 50, and on into the coupler lumen 54 consistent with the axial flow path 70' and bypass tubing 3b.

Figure 16:
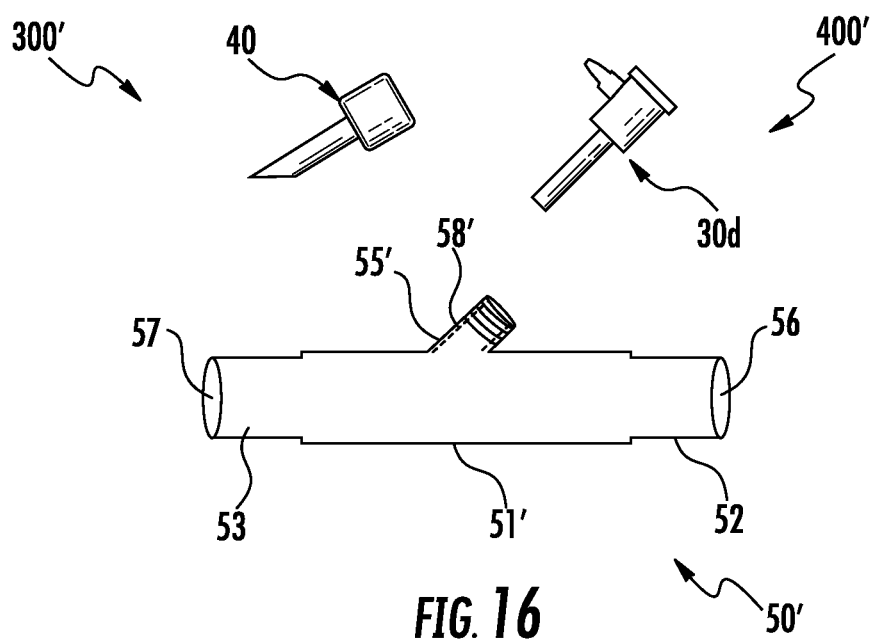
FIG. 16 is another embodiment of a tubing connector of the present invention.
Figure 17A:
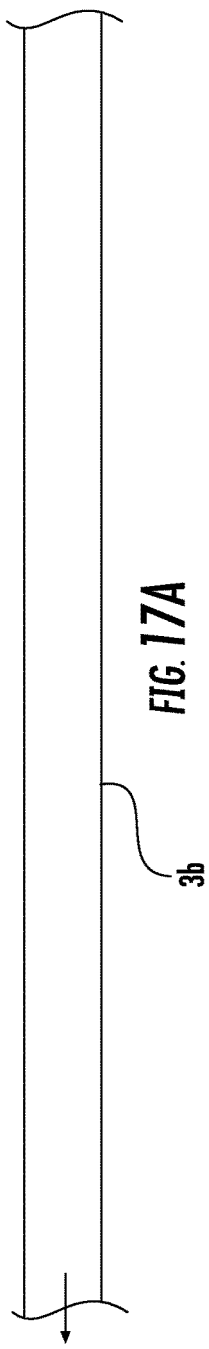
FIG. 17A depicts standard bypass tubing before insertion of a tube coupler.

In other embodiments, as seen in FIG. 16, the tube coupler 50' includes an angled access port 55', such as the angled side port 25 previously described in connection with the modified cannula 24. Accordingly, it should be appreciated that the tube coupler 50, 50' may include a traditional access port 55 or angled access port 55' providing an access point to the interior of the tube coupler 50, 50', and therefore, the endovascular system. The angled access port 55' is located along the coupler body 51 of the tube coupler 50', and may have any angle relative to the coupler body 51 as may promote ease of insertion of intervention devices 60. For instance, as previously discussed, the angle of the angled access port 55' may be any angle between 0° up to 90°. The angled access port 55' extends from the coupler body 51 and defines an angled access port channel 58' extending through at least a portion of the interior of the angled access port 55', which is in fluid communication with the coupler lumen 54 at one end, and has an opening at the other end for receiving an adaptor/insertion cap 30*d* and/or shaft 33*d* as previously described. Accordingly, the angled access port channel 58' provides exterior access to the coupler lumen 54 and axial flow path 70" therein such that a wire, catheter or other intervention device 60 may be inserted through a hemostatic membrane 36 within such adaptor 30*d*, as previously described, and be inserted into the access port channel 58' and axial flow path 70" of the tube coupler 50', and on into the coupler lumen 54 and bypass tubing 3*b*, as shown in FIG. 17F.

The tube coupler 50' may also coordinate with the adaptor/insertion cap 30*d* and occlusive cap 40 as previously described, either to provide endovascular access through the tube coupler 50' or to seal off and occlude the angled access port 55' when access is not desired. Accordingly, the tube coupler 50, 50' may comprise a part of a vascular access system 400, 400', respectively, in conjunction with an adaptor 30 as described herein, such as in FIG. 17F. The tube coupler 50, 50' may also be part of an occlusion system 300' in conjunction with a occlusive cap 40, as in FIG. 17C. The angled access port 55' of the tube coupler 50' can also be used to establish a secondary circuit for distal perfusion, as previously described.

FIGS. 17A-17F demonstrate the steps of inserting a tube coupler 50, 50' into an already established ECLS system. A tube coupler 50' with angled access port 55' is shown, but it should be appreciated that a tube coupler 50 with a right angle access port 55 would be inserted in a similar manner. To begin, as in FIG. 17A, a location along the bypass tubing 3*b* where the tube coupler 50' is to be inserted is identified. This location may be anywhere in the bypass system, but is preferably on the arterial side of the bypass system. In at least one embodiment, the location is proximate to, and upstream or proximal to, the location for intervention device use.

Figure 17B:
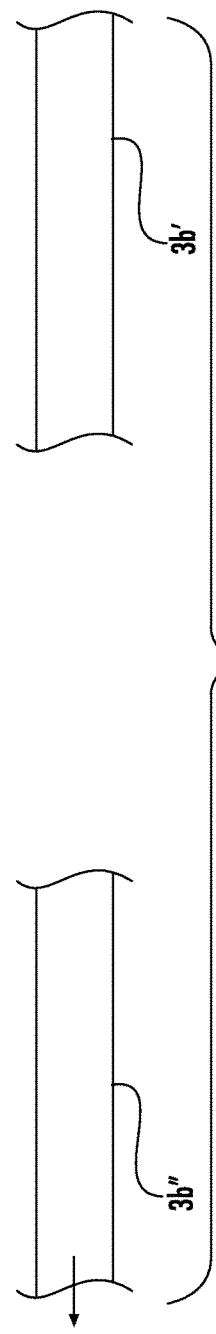
FIG. 17B depicts the tubing of FIG. 17A cut in preparation of receiving a coupler.

Once an insertion location is identified, the bypass system is temporarily interrupted, such as by clamping, crimping or otherwise restricting the bypass tubing 3*b* on either side, or at least upstream of, the insertion location. This prevents the flow of blood through the ECMO system, and allows the tubing to be cut without loss of blood. The bypass tubing 3*b* is then cut downstream of the restriction point, resulting in two pieces of bypass tubing, as seen in FIG. 17B. The proximal piece 3*b*' of bypass tubing is located with the restriction point, and is closer to the pump of the ECMO system. The distal piece 3*b*" of bypass tubing is located downstream of the cut in the tubing, and is closer to the arterial incision 12 where the bypass system is reintroduced back into the subject or patient.

Figure 17C:
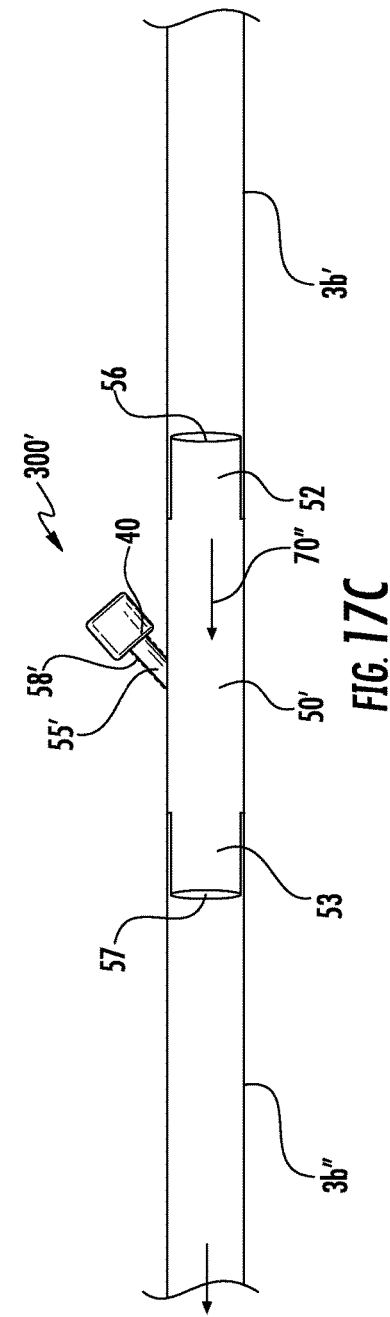
FIG. 17C shows a coupler placed between sections of bypass tubing, where a cap is in place.

Once the tubing 3*b* is cut, the tube coupler 50' is then inserted between the proximal piece 3*b*' and distal piece 3*b*" of bypass tubing, as shown in FIG. 17C. For instance, the first end 52 of the tube coupler 50' is joined to the proximal piece 3*b*' of the bypass tubing, and the opposite second end 53 of the tube coupler 50' is joined to the distal piece 3*b*" of bypass tubing. The first and second ends 52, 53 of the tube coupler 50' will be oriented such that the angled access port 55' opens toward the proximal piece 3*b*' of bypass tubing, such that an intervention device 60 inserted therein is directed toward the distal piece 3*b*" and toward the heart of the subject. When the tube coupler 50' is first inserted and joined to the proximal and distal pieces 3*b*', 3*b*" of the bypass tubing, a occlusive cap 40 may already be inserted in the angled side port 25 in a fully occluding position.

Once the bypass tubing is joined and a hemostatic seal is established at the first and second ends 52, 53, the clamp or other restriction device temporarily interrupting the flow through the bypass system is removed, and flow through the system is re-established. The coupler lumen 54 is in fluid communication with both the proximal piece 3*b*' and distal piece 3*b*" of bypass tubing, defining a flow path with the tubing such that as blood flows through the bypass tubing it enters the proximal piece 3*b*', then the coupler lumen 54, then the distal piece 3*b*" of bypass tubing on its path from the oxygenator to the patient's heart. When the occlusive cap 40 is included in the angled access port 55' of a tube coupler 50', or when a standard cap is inserted in the right angle access port 55 of a tube coupler 50, the access port channel 58, 58' is occluded and blood is prevented from pooling and stagnating in the access port 55, 55'.

When access to the bypass system is desired, such as to establish a secondary circuit as previously described or to gain endovascular access for medical intervention, the occlusive cap 40 may be removed from the access port 55, 55', as depicted in FIG. 17D. An adaptor 30*d*, as previously described, is then inserted and attached to the access port 55, 55', as shown in FIG. 17E. Once the adaptor 30*d* is in place, an intervention device 60 such as a wire or catheter or other suitable device may be inserted into the tube coupler 50', as in FIG. 17F. Specifically, the intervention device 60 enters through the membrane 36 of the adaptor 30*d* and continues to advance through the shaft 33*d*, into the coupler lumen 54, and on into the distal piece 3*b*" of bypass tubing until the particular site for intervention is reached.

In at least one embodiment, as described above with reference to FIGS. 17A-17F, the tube coupler 50, 50' may be inserted, such as spliced, into an already established ECLS system, such as an ECMO system. In other embodiments, the tube coupler 50, 50' may be included in an ECLS system when it is being assembled for use. It may take the place of an arterial cannula 4, and it may be used in conjunction with an arterial cannula 4 or a modified cannula 24 as described above. In at least one embodiment, as shown in FIG. 18, the bypass system may include one or more couplers 50, 50' in series in the bypass tubing 3*b*, so that multiple intervention devices 60 can gain access to the endovascular system at the same time, such as when multiple devices are needed to perform an endovascular procedure. Each tube coupler 50, 50' provides one access point to the system, and as many couplers 50, 50' can be include in the system as may be needed for a particular procedure. In other embodiments, each tube coupler 50, 50' may also have more than one access port 55, 55', as shown in FIG. 19, where each access port 50, 50' provides entry for one insertion device 60, such as a wire or catheter, or an occlusive occlusive cap 40, or establishing a secondary circuit for distal perfusion.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents. Now that the invention has been described,

What is claimed is:

1. A system for vascular access, comprising:
a cannula having a cannula lumen therein establishing an axial flow path and a side port extending at a right angle from said cannula having a side port channel extending at a right angle from said cannula lumen and providing exterior access to said cannula lumen through a right angle; and
an adaptor securable to said side port and having a shaft inserted in said side port channel and protruding into said cannula lumen and providing exterior access to said cannula lumen through an adaptor lumen in said shaft, said adaptor lumen receiving an intervention device inserted therein, said adaptor lumen having a curved configuration with a distal terminal opening exposed within said cannula lumen and oriented toward said axial flow path to modify an angle of insertion of said intervention device through said adaptor lumen thereby directing said intervention device within said cannula lumen through the right angle extension of said side port channel in a direction consistent with said axial flow path, said shaft including a flange extending radially therefrom, said flange abutting a lip of said cannula side port, and a connector selectively restraining said adaptor to said cannula side port and said flange positioned between said lip of said cannula side port and said connector.

2. The system according to claim 1, wherein said connector is a floating Luer connector.

3. The system according to claim 1, wherein said adaptor includes a cavity facing said connector and correspondingly receiving at least a portion of said connector.

4. The system according to claim 1, wherein said adaptor further includes an insertion cap removably secured to said side port for closing off said side port, said insertion cap having a side arm extending therefrom and having an unobstructed side arm passage in fluid communication with said adaptor lumen and said cannula lumen to selectively vent air from said system.

5. The system according to claim 1, wherein said curved configuration of said adaptor lumen includes at least one straight segment.

6. The system according to claim 1, further comprising a membrane at an exterior of said adaptor lumen and permitting passage of said intervention device therethrough.

7. The system according to claim 6, wherein said shaft extends opposite of said membrane.

* * * * *